United States Patent
Lynch

(10) Patent No.: US 7,473,678 B2
(45) Date of Patent: Jan. 6, 2009

(54) PLATELET-DERIVED GROWTH FACTOR COMPOSITIONS AND METHODS OF USE THEREOF

(75) Inventor: Samuel E. Lynch, Franklin, TN (US)

(73) Assignee: Biomimetic Therapeutics, Inc., Franklin, TN (US)

( * ) Notice: Subject to any disclaimer, the term of this patent is extended or adjusted under 35 U.S.C. 154(b) by 239 days.

(21) Appl. No.: 11/159,533

(22) Filed: Jun. 23, 2005

(65) Prior Publication Data

US 2006/0084602 A1 Apr. 20, 2006

Related U.S. Application Data

(63) Continuation-in-part of application No. 10/965,319, filed on Oct. 14, 2004, now abandoned.

(51) Int. Cl.
 A61K 38/00 (2006.01)
 A61K 38/16 (2006.01)
 C12N 15/00 (2006.01)

(52) U.S. Cl. .................. 514/2; 424/198.1; 424/423; 435/69.1

(58) Field of Classification Search .................. None
See application file for complete search history.

(56) References Cited

U.S. PATENT DOCUMENTS

| | | |
|---|---|---|
| 3,943,072 A | 3/1976 | Thomson et al. |
| 4,845,075 A | 7/1989 | Murray et al. |
| 4,861,757 A | 8/1989 | Antoniades et al. |
| RE33,161 E | 2/1990 | Brown et al. |
| 4,904,259 A | 2/1990 | Itay |
| RE33,221 E | 5/1990 | Brown et al. |
| 4,963,145 A | 10/1990 | Takagi et al. |
| 4,975,526 A | 12/1990 | Kuberasampath et al. |
| 5,013,649 A | 5/1991 | Wang et al. |
| 5,019,559 A | 5/1991 | Antoniades et al. |
| 5,034,375 A | 7/1991 | Antoniades et al. |
| 5,053,212 A | 10/1991 | Constantz et al. |
| 5,106,748 A | 4/1992 | Wozney et al. |
| 5,108,922 A | 4/1992 | Wang et al. |
| 5,116,738 A | 5/1992 | Wang et al. |
| 2,124,316 A | 6/1992 | Antoniades et al. |
| 5,124,316 A | 6/1992 | Antoniades et al. |
| 5,128,321 A * | 7/1992 | Murray et al. .............. 514/12 |
| 5,129,905 A | 7/1992 | Constantz |
| 5,141,905 A | 8/1992 | Rosen et al. |
| 5,149,691 A * | 9/1992 | Rutherford .............. 514/12 |
| 5,165,938 A | 11/1992 | Knighton |
| 5,187,076 A | 2/1993 | Wozney et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,376,636 A | 12/1994 | Rutherford et al. |
| 5,457,093 A * | 10/1995 | Cini et al. .............. 514/12 |
| 5,518,680 A | 5/1996 | Cima et al. |
| 5,531,794 A | 7/1996 | Takagi et al. |
| 5,549,123 A | 8/1996 | Okuyama et al. |
| 5,635,372 A | 6/1997 | Celeste et al. |
| 5,650,176 A | 7/1997 | Lee et al. |
| 5,747,273 A | 5/1998 | Khosravi et al. |
| 5,783,217 A | 7/1998 | Lee et al. |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,077,989 A | 6/2000 | Kandel et al. |
| 6,136,029 A | 10/2000 | Johnson et al. |
| 6,221,625 B1 | 4/2001 | Ashihara et al. |
| 6,224,635 B1 * | 5/2001 | Ricci et al. .............. 623/23.62 |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |

(Continued)

FOREIGN PATENT DOCUMENTS

| | | |
|---|---|---|
| EP | 00530804 A1 | 3/1993 |
| EP | 0741785 | 11/1996 |
| EP | 0 479 799 B1 | 8/1997 |
| EP | 00741785 | 11/1999 |
| EP | 01025871 A1 | 8/2000 |

(Continued)

OTHER PUBLICATIONS

Nevins et al., J. Periodontol., 2003 Sept..; 74(9):1282-1292.*
Heini et al., Eur. Spine J., 2001, 10:S205-213.*
Arm, D.M. et al., "Effect of Controlled Release of Platelet-derived Growth Factor from a Porous Hydroxyapatite Implant on Bone Ingrowth," *Biomaterials*, 1996, 17:703-709.
Cho, Moon II et al., "Platelet-derived Growth Factor-Modulated Guided Tissue Regenerative Therapy," Department of Oral Biology and Periodontal Disease Research Center School of Dental Medicine, State University of New York at Buffalo, Buffalo, NY, *J. Periodontal*, June 1995, 66(6).

(Continued)

*Primary Examiner*—Elizabeth C. Kemmerer
*Assistant Examiner*—Xiaozhen Xie
(74) *Attorney, Agent, or Firm*—Morrison & Foerster LLP

(57) ABSTRACT

A method for promoting growth of bone, periodontium, ligament, or cartilage in a mammal by applying to the bone, periodontium, ligament, or cartilage a composition comprising platelet-derived growth factor at a concentration in the range of about 0.1 mg/mL to about 1.0 mg/mL in a pharmaceutically acceptable liquid carrier and a pharmaceutically-acceptable solid carrier.

45 Claims, 2 Drawing Sheets

U.S. PATENT DOCUMENTS

| | | |
|---|---|---|
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,743,232 B2 | 6/2004 | Overaker et al. |
| 6,866,991 B2 | 3/2005 | Gilbertson et al. |
| 6,903,078 B1* | 6/2005 | Williams ............ 514/44 |
| 6,972,130 B1 | 12/2005 | Lee et al. |
| 7,005,135 B2 | 2/2006 | Janas et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,604 B2 | 3/2007 | Brown et al. |
| 2001/0014682 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2002/0004225 A1 | 1/2002 | Hart et al. |
| 2002/0018796 A1 | 2/2002 | Wironen |
| 2002/0037799 A1 | 3/2002 | Li et al. |
| 2002/0082220 A1 | 6/2002 | Hoemann et al. |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2003/0006025 A1 | 1/2003 | Manini et al. |
| 2003/0049328 A1* | 3/2003 | Dalal et al. ............ 424/602 |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0105015 A1 | 8/2003 | Gilbertson et al. |
| 2003/0152606 A1 | 8/2003 | Gerber |
| 2003/0193106 A1 | 10/2003 | Yu et al. |
| 2003/0199615 A1 | 10/2003 | Chaput et al. |
| 2003/0228364 A1* | 12/2003 | Nathan ............ 424/486 |
| 2004/0002770 A1* | 1/2004 | King et al. ............ 623/23.51 |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0076685 A1 | 4/2004 | Tas |
| 2004/0078090 A1 | 4/2004 | Binette et al. |
| 2004/0197311 A1 | 10/2004 | Brekke et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0031694 A1 | 2/2005 | Gilbertson et al. |
| 2005/0074461 A1 | 4/2005 | Brekke et al. |
| 2005/0107162 A1 | 5/2005 | Kilby et al. |
| 2005/0107887 A1 | 5/2005 | Tate et al. |
| 2005/0119754 A1 | 6/2005 | Trieu et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |
| 2006/0084602 A1 | 4/2006 | Lynch |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0247156 A1 | 11/2006 | Vanderby et al. |
| 2007/0003752 A1 | 1/2007 | Bruce et al. |
| 2007/0053951 A1 | 3/2007 | Gonzalez et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0218098 A1 | 9/2007 | Reif et al. |
| 2007/0244484 A1 | 10/2007 | Luginbuehl |
| 2001/0038848 A1 | 11/2007 | Donda et al. |
| 2007/0282455 A1 | 12/2007 | Luginbuehl et al. |
| 2006/0149392 A1 | 7/2008 | Hsieh et al. |

FOREIGN PATENT DOCUMENTS

| | | |
|---|---|---|
| EP | GB 02367497 A | 4/2002 |
| EP | 00896825 B1 | 7/2002 |
| EP | 01234552 B1 | 8/2002 |
| EP | 01146897 B1 | 9/2002 |
| EP | 1242129 | 9/2002 |
| EP | 01100488 B1 | 4/2003 |
| EP | 00994694 B1 | 10/2003 |
| EP | 01374857 A1 | 1/2004 |
| EP | 01410811 A1 | 4/2004 |
| EP | 01561481 A2 | 8/2005 |
| EP | 1563846 | 8/2005 |
| EP | 01583846 A1 | 8/2005 |
| EP | 01681067 A1 | 7/2006 |
| EP | 1 712 244 | 10/2006 |
| EP | 01719531 A2 | 11/2006 |
| EP | 01719532 A2 | 11/2006 |
| JP | 7-250688 | 10/1995 |
| JP | 2003-265592 A | 9/2003 |
| WO | WO 1992/009301 A1 | 6/1992 |
| WO | WO 1992/016181 A2 | 10/1992 |
| WO | WO 1993/000432 A1 | 1/1993 |
| WO | WO 1993/005808 A1 | 4/1993 |
| WO | WO 1993/009229 A1 | 5/1993 |
| WO | WO 1993008825 A1 | 5/1993 |
| WO | WO 1993/016099 A2 | 8/1993 |
| WO | WO 1993/020859 | 10/1993 |
| WO | WO 1994001557 A1 | 1/1994 |
| WO | WO 1994/005800 A1 | 3/1994 |
| WO | WO 1994/015949 A1 | 7/1994 |
| WO | WO 1994/015965 A1 | 7/1994 |
| WO | WO 1994/015966 A1 | 7/1994 |
| WO | WO 1994/021681 A1 | 9/1994 |
| WO | WO 1994/022463 | 10/1994 |
| WO | WO 1994/026892 A1 | 11/1994 |
| WO | WO 1994/026893 A1 | 11/1994 |
| WO | WO 1994/028889 A1 | 12/1994 |
| WO | 1995/001801 A1 | 1/1995 |
| WO | WO 1995/001802 A1 | 1/1995 |
| WO | WO 1995/007982 A1 | 3/1995 |
| WO | WO 1995/010539 A1 | 4/1995 |
| WO | WO 1995/016035 A3 | 6/1995 |
| WO | WO 1995/018856 A1 | 7/1995 |
| WO | WO 1995/020967 | 8/1995 |
| WO | WO 1995/028950 | 11/1995 |
| WO | WO 1996/001845 A1 | 1/1996 |
| WO | WO 1996/002559 A1 | 2/1996 |
| WO | WO 1996/016668 A1 | 6/1996 |
| WO | WO 1996/017924 A2 | 6/1996 |
| WO | WO 1998/000183 A2 | 1/1998 |
| WO | WO 1998/041246 A2 | 9/1998 |
| WO | WO 1998/051354 A2 | 11/1998 |
| WO | WO 1999/030726 | 6/1999 |
| WO | WO 1999/038543 A2 | 8/1999 |
| WO | WO 1999/067289 | 12/1999 |

| | | |
|---|---|---|
| WO | WO 2001/032197 | 5/2001 |
| WO | WO 2001/035932 | 5/2001 |
| WO | WO 2001/041822 | 6/2001 |
| WO | WO 2001/060424 | 6/2001 |
| WO | WO 2001/057083 A1 | 8/2001 |
| WO | WO 2001/060424 | 8/2001 |
| WO | WO 2001/066044 | 9/2001 |
| WO | WO 2001/066130 | 9/2001 |
| WO | WO 2001/068135 | 9/2001 |
| WO | WO 2002/000244 A2 | 1/2002 |
| WO | WO 2002/000272 A3 | 1/2002 |
| WO | WO 2002/036147 A1 | 5/2002 |
| WO | WO 2002/062405 | 8/2002 |
| WO | WO 2002/067978 A1 | 9/2002 |
| WO | WO 2002/102783 | 12/2002 |
| WO | WO 2003/006025 | 1/2003 |
| WO | WO 2003/043576 A2 | 5/2003 |
| WO | WO 2003/070186 | 8/2003 |
| WO | WO 2004/002539 A2 | 1/2004 |
| WO | WO 2004/010907 A1 | 2/2004 |
| WO | WO 2004/071543 A1 | 8/2004 |
| WO | WO 2005/046746 | 11/2004 |
| WO | WO 2004/110308 A2 | 12/2004 |
| WO | WO 2005/009496 | 2/2005 |
| WO | WO 2005/032461 | 4/2005 |
| WO | WO 2006/031388 A2 | 3/2006 |
| WO | WO 2006/044334 A2 | 4/2006 |
| WO | WO 2006/093808 A1 | 9/2006 |
| WO | WO 2007/061889 A2 | 5/2007 |
| WO | WO 2007/087436 A2 | 8/2007 |
| WO | WO 2007/089997 A2 | 8/2007 |
| WO | WO 2007/090102 A2 | 8/2007 |

OTHER PUBLICATIONS

Hsu, M.D., Charles et al., "Clinical Implications of Growth Factors in Flexor Tendon Wound Healing," *The Journal of Hand Surgery*, Jul. 2004, 29(4).

Mitlak, B.H. et al., "The Effect of Systemically Administered PDGF-BB on the Rodent Skeleton," *Journal of Bone and Mineral Research*, 1996, 11(2).

Nakamura, N. et al., "Early Biological Effect of In Vivo Gene Transfer of Platelet-derived Grown Factor (PDGF)-B into Healing Patellar Ligament," *Gene Therapy*, 1998, 5:1165-1170.

Nevins, M. et al., "Periodontal Regeneration in Humans Using Recombinant Human Platelet-derived Growth Factor-BB (RhPDGF-BB) and Allogenic Bone," *J. Periodontal*, Sept. 2003, 74(9).

Rasubala, L. et al., "Platelet-derived Growth Factor and Bone Morphogenetic Protein in the Healing of Mandibular Fractures in Rats," *British Journal of Oral and Maxillofacial Surgery*, 2003, 41:173-178.

Solheim, E., "Growth Factors in Bone," *International Orthopedics- (SICOT)*, 1998, 22:410-416.

Spindler, K.P. et al., "Patellar Tendon and Anterior Curciate Ligament Have Different Mitogenic Responses to Platelet-derived Growth Factor and Transforming Growth Factor B." *Journal of Orthopedic Research*, 1996, 14:542-546.

Adalberto et al., "Periodontal Regeneration," J. Periodontal, 2005, 76(9): 1601-1622.

Aghaloo, T.L. DDS MD et al., "Evaluation of Platelet-Rich Plasma in Combination with A-rganic Bovine Bone in the Rabbit Cranium: A Pilot Study," The International Journal of Oral and Maxillofacial Implants, 2004, 19:59-65.

Anitua, E. et al., "Autologous platelets as a source of proteins for healing and tissue regeneration," Thromb Haemost, 2004, 91:4-15.

Anusaksathien et al., "Effect of Sustained Gene Delivery of Platelet-Derived Growth Factor or Its Antagonist (PDGF - 1308) ib Tissue-Engineered Cementum," J. Periodontal, 2004, 75(3): 429-440.

Anusaksathien et al., "Growth Factor Delivery to Re-Engineer Periodontal Tissues," Current Pharmaceutical Biotechnology, 2002, vol. 3(2): 129-139.

Anusaksathien et al., "Platelet-Derived Growth Factor Gene Delivery Stimulates ex Vivo Gingival Repair," Tissue Engineering, 2003, 9(4): 745-756.

Arm, et al. Effect of Controlled Release of Platelet-derived Growth Factor from a Porous Hydroxyapatite Implant on Bone Ingrowth, Biomaterials 17 (1996) 703-709.

Babbush, C.A. DDS MSCD et al., "An In Vitro and In Vivo Evaluation of Autologous Platelet Concentrate in Oral Reconstruction," Implant Dent., 2003, 12:24-34.

Bateman, et al. Platelet-Derived Growth Factor Enhancement of Two Alloplastic Bone Matrices, J. Periodontol. (2005) 76: 1833-1841.

BMP Gene Delivery for Alveolar Bone Engineering at Dental Implant Defects - Molecular Therapy, vol. 11, -. Feb. 2, 2005.

Bolander, "Regulation of Fracture Repair by Growth Factors," *P.S. E.B.M.*, 1992, 200: 165-170.

Camargo, et al, "Platelet-rich plasma and bovine porous bone mineral combined with guided tissue regeneration in the treatment of intrabony defects in humans," J Periodont Res 2002, 37: 300-306.

Camargo, L.V. PM et al., "Effectiveness of a combination of platelet-rich plasma, bovine porous bone mineral and guided tissue regeneration in the treatment of mandibular grade II molar furcations in humans," J. Clin. Periodontol, 2003, 30:746-751.

Camelo et al., "Clinical radiographic, and histologic evaluation of human periodontal defects treated with bio-oss and bio-guide," International Journal of Periodontics and Restorative Dentistry, 1998, 18(4): 321-332.

Camelo et al., "Periodontal regeneration with an autoge-us bone-bio-oss composite graft and a bio-guide membrane," International Journal of Periodontics and Restorative Dentistry. 2001, 21(2): 109-120.

Canalis, "Effect of Growth Factors on Bone Cell Replication and Differentiation," *Clinical Orthopedics and Related Research*, 1985, 193: 246-263.

Chen et al., "Ade-viral Gene Transfer of PDGF Downregulates Gas Gene Product PDGFR and Prolongs ERK and Akt/PKB Activation," Am J Physiol Cell Physiol 282: C538-C544, 2002.

Cho et al., "Platelet-derived Growth Factor - Modulated Guided Tissue Regenerative Therapy," J Periodontal, 1995, 66(6): 522-530.

Cochran, et al. "Effects of Platelet-Derived Growth Factor Isoforms on Calcium Release From Neonatal Mouse Calvariae," Bone, 1993, 14: 53-58.

Cooke et al., "Effect of rhPDGR-BB Delivery on Mediators of Periodontal Wound Repair," Tissue Engineering, 2006, 12(6): 1441-1450.

Fennis, et al, "Mandibular reconstruction: A clinical and radiographic animal study on the use of autoge-us scaffolds and platelet-rich plasma," Int. J. Oral Maxillofac. Surg., 2001, 31:281-286.

Fennis, et al, "Mandibular reconstruction: a histological and histomorphometric study on the use of autoge-us scaffolds, particulate cortico-cancellous bone grafts and platelet rich plasma in goats," Int. J. Oral Maxillofac. Surg., 2004, 33:48-55.

Fontana, et al, "Effect of Platelet-Rich Plasma on the Peri-implant Bone Response: An Experiment Study," Implant Dentistry, 2004, 13: 73-78.

Garg, "The Use of Platelet-Rich Plasma to Enhance the Success of Bone Grafts Around Dental Implants," Dental Implantology Update, 2000, 11(3): 41-44.

Giannobile et al., "Comparison of Canine and -n-Human Primate Animal Models for Periodontal Regenerative Therapy: Results Following a Single Administration of PDGF/IGF-l.," J. Periodontol 1994, 65:1158-1168.

Giannobile et al., "-n-Coordinate Control of Bone Formation Displayed by Growth Factor Combinations with IGF-l," J Dent Res, 1997, 76(9): 1569-1578.

Giannobile et al., "Periodontal Tissue Engineering by Growth Factors," Bone, 1996, 19, Supplement: 23S-37S.

Giannobile et al., "Recombinant Human Osteogenic Protein-1 (OP-1) Stimulates Periodontal Wound Healing in Class III Furcation Defects," J Periodontol, 1998, 69:129-137.

Giannobile, "Platelet-Derived Growth Factor (PDGF) Gene Delivery for Application in Periodontal Tissue Engineering," J Periodontol, 2001, 72: 815-823.

Gilbertson et al., "Platelet-derived Growth Factor C (PDGF-C), a -vel Growth Factor That Binds to PDGF a and b Receptor," The Journal of Biological Chemistry, 2001, 276(29): 27406-27414.

Grageda, "Platelet-Rich Plasma and Bone Graft Materials: A Review and a Standardized Research Protocol," Implant Dentistry, 2004, 13(4): 301-309.

Green et al., "Immunolocalization of platelet-derived growth factor A and B chains and PDGF- and receptors in human gingival wounds," Journal of Periodontal Research, 1997, 32(2): 209-214.

Gronwald et al., "Cloning and expression of a cDNA coding for the human platelet-derived growth factor receptor: Evidence for more than one receptor class," Proc. Natl. Acad. Sci. USA, 1988, 85: 3435-3439.

Hart et al., "Purification of PDGF-AB and PDGF-BB from Human Platelet Extracts and Identification of All Three PDGF Dimers in Human Platelets," Biochemistry, 1990, 29: 166-172.

Hart et al., "Synthesis, Phosphorylation, and Degredation of Multiple Forms of the Platelet-derived Growth Factor Receptor Studied Using a Mo-clonal Antibody," The Journal of Biological Chemistry, 1987, 262(22): 10780-10785.

Hart et al., "Two Classes of PDGF Receptor Recognize Different Isoforms of PDGF," Science, 1988, 240: 1529-1531.

Hollinger, J.O. et al., "Therapeutic Opportunities for Bone Grafting," Mar. 5, 2006.

Howell et al.. "A Phase I/II Clinical Trial to Evaluate a Combination of Recombinant Human Platelet-Derived Growth Factor-BB and Recombinant Human Insulin-Like Growth Factor-I in Patients with Period. Dis.," J. Periodontol., 1997, 68(12): 1186-1193.

Howes et al., "Platelet-Derived Growth Factor Enhances Demineralized Bone Matrix-Induced Cartilage and Bone Formation," *Calcif Tissue Int.*, 1988, 42: 34-38.

Hsu, MD. et al., "Clinical Implications of Growth Factors in Flexor Tendon Wound Healing, " The Journal of Hand Surgery, 2004, 29(4): 551-563.

Ikezawa et al., "Characterization of Cementum Derived Growth Factor as an Insulin-Like Growth Factor-l Like Molecule," Connective Tissue Research, 1997, 36(4): 309-319.

Jensen et al, "Platelet rich plasma and fresh frozen bone allograft as enhancement of implant fixation - An experimental study in dogs," Journal of Orthopaedic Research, 2004, 22: 653-658.

Jiang et al., "Modification of an Osteoconductive A-rganic Bovine Bone Mieral Matrix with Growth Factors," J. Periodontol., 1999, 70(8): 834-839.

Jin et al., "Engineering of Tooth-Supporting Structures by Delivery of PDGF Gene Therapy Vectors," Molecular Therapy, 2004, 9: 519-526.

Kaigler, "Growth factor delivery for oral and periodontal tissue engineering," Expert Opin Drug Deliv., 2006, 3(5): 1742-5247.

Kassolis et al., "Alveolar Ridge and Sinus Augmentation Utilizing Platelet-Rich Plasma in Combination with Freeze-Dried Bone Allograft: Case Seris," Journal of Periodontology, 2000, 71(10):1654-1661.

Kazlauskas, et al. Different effects of homo- and heterodimers of platelet-derived growth factor A and B chains on human and mouse fibroblasts, The EMBO Journal (1988) 7 (12): 3727-3735.

Kim et al, "A Comparative Study of Osseointegration of Avana in a Demineralized Freeze-Dried Bone Alone or With Platelet-Rich Plasma," J Oral Maxillofac Surg, 2002, 60:1018-1025..

Kim et al, "Use of Particulate Dentin-Plaster of Paris Combination with/without Platelet-Rich Plasma in the Treatment of Bone Defects Around Implants," The International Journal of Oral & Maxillofacial Implants, 2002; 17:86-94.

Kovacs et al, "Comparative Study of b-Tricalcium Phosphate Mixed with Platelet-Rich Plasma versus b-Tricalcium Phosphate, A Bone Substitute Material in Dentistry," Acta Veterinaria Hungarica, 2003, 51(4):475-484.

Landesberg et al, "Quantification of Growth Factor Levels Using a Simplified Method of Platelet-Rich Plasma Gel Preparation," J. Oral Maxillofac Surg, 2000, 58: 297-300.

Lasa et al, "Delivery of Demineralized Bone Powder by Fibrin Sealant," Plast. Reconstr. Surg., 1995, 96: 1409.

Lekovic, et al, "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," J Periodontol, 2002: 73.

Lioubavina-Hack et al., "Effect of Bio-Oss with or without platelet-derived growth factor on bone formation by 'guided tissue regeneration': a pilot study in rats," J Clin. Periodontol, 2003, 32: 1254-1260.

Lioubavina-Hack et al., "Methyl cellulose gel obstructed bone formation by GBR: an experimental study in rats," H. Clin. Periodontol., 2005, 32: 1247-1253.

Maiorana et al, "Maxillary Sinus Augmentation with A-rganic Bovine (Bio-Oss) and Autologous Platelet-Rich Plasma: Preliminary Clinical and Histologic Evaluations," J Periodontics Restorative Den, 2003, 23: 227-235.

McAllister et al., "Eighteen-month Radiographic and Histologic Evaluation of Sinus Grafting with A-rganic Bovine Bone in the Chimpanzee," The International Journal of Oral & Maxillofacial Implants, 1999, 14(3): 361-368.

Mitlak et al., "The Effect of Systemically Administered PDGF-BB on the Rodent Skeleton," Journal of Bone and Mineral Research, 1996, 11(2): 238-247.

Nevia et al., "The Effect of Platelet-Rich Plasma on the Coronally Advanced Flap Root Coverage Procedure: A Pilot Human Trial," J. Periodontal, 2005, 76(10): 1768-1777.

Nevins et al., "Periodontal Regeneration in Humans Using Recombinant Human Platelet-derived Growth Factor-BB (rhPDGF-BB) and Allogenic Bone," J. Periodontal, 2003, 74(9): 1282-1292.

Nevins et al., "Platelet-Derived Growth Factor Stimulates Bone Fill and Rate of Attachment Level Gain: Results of a Large Multicenter Randomized Controlled Trial," J. Periodontal, 2005, 76(12): 2205-2215.

Philippart et al., "Human Recombinant Tissue Factor, Platelet-rich Plasma, and Tetracycline Induce a High-Quality Human Bone Graft: A 5-year Survey," The International Journal of Oral and Maxillofacial Implants, 2003, 118: 411-416.

Rasubala et al., "Platelet-derived Growth Factor and Bone Morphogenetic Protein in the Healing of Mandibular Fractures in Rats," British Journal of Oral and Maxillofacial Surgery, 2003, 41: 173-178.

Rodriguez et al., "Maxillary Sinus Augmentation with Deproteinated Bovine Bone and Platelet Rich Plasma with Simultaneous insertion of Endosseous Implants," J. Oral Maxillofac. Surg., 2003, 61:157-163.

Sandberg, "Matrix in Cartilage and Bone Development: Current Views on the Function and Regulation of Major Organic Components," *Annals of Medicine*, 1991, 23: 207-217.

Sarment et al., "Effect of rhPDGF-BB on Bone Turnover During Periodontal Repair," J. Clin Periodontol, 2006, 33: 135-140.

Saygin et al., "Molecular and Cell Biology of Cementum," Periodontology, 2000, 24: 73-98.

Schmitt et al., "A review of the effects of insulin-like growth factor and platelet derived growth factor on in vivo cartilage healing and repair," Osteoarthritis and Cartilage, 2006, 14(5): 403-412.

Solheim, "Growth Factors in Bone," International Orthopaedics (SICOT), 1998, 410-416.

Stephan et al., "Platelet-Derived Growth Factor Enhancement of a Mineral-Collagen Bone Substitute," J. Periodontol, 2000, 71: 1887-1892.

Suba et al., "Facilitation of b-Tricalcium Phosphate-Induced Aveolar Bone Regeneration by Platelet-Rich Plasma in Beage Dogs: A Histologic and Histomorphometric Study," The International J. of Oral and Maxillofacial Implants, 2004, 19(6):832-838.

Visnapuu et al., "Distribution of fibroblast growth factors (FGFR-1 and -3) and platelet-derived growth factor receptors (PDGFR) in the rat mandibular condyle during growth," *Orthod. Craniofacial*, 2002, 5: 147 - 153.

Wei et al., "Na-Fibrous Scaffold for Controlled Delivery of Recombinant Human PDGF-BB," Journal of Controlled Release, 2006, 112: 103-110.

Williams et al., "Tissue Engineering: What Does It Mean? Why Is It Important?" Compendium, 2005, 26(1): 54-60.

Yazawa et al, "Basic Studies on the Clinical Applications of Platelet-Rich Plasma," Cell Transplantation, 2003, 12: 509-518.

Zhu et al., "Gene Transfer and Expression of Platelet-Derived Growth Factors Modulate Periodontal Cellular Activity," J. Dent Res, 2001, 80(3):892-897.

Lee et al., "The bone regenerative effect of platelet-derived growth factor-BB delivered with a chitosan/tricalcium phosphate sponge carrier," J. Periodontol., 2000, 71(3): 418-424.

Lee et al., "Enhanced bone formation by controlled growth factor delivery from chitosan-based biomaterials," Journal of Controlled Release, 2002, 78: 187-197.

U.S. Appl. No. 10/965,319, filed Oct. 14, 2004, inventor Lynch

Antoniades et al., "Human platelet-derived growth factor (PDGF): amino-terminal amino acid sequence" Science, 1983, 220: 963-965.

Betsholtz et al., "cDNA sequence and chromosomal localization of human platelet-derived growth factor A-chain and its expression in tumor cell lines" Nature, 1986, 320: 695-699.

Clergeau et al., "Healing Response to Anorganic Bone implantation in Periodontal Intrabony Defects in Dogs. Partl. Bone Regeneration. A Microradiographic Study" J. Periodontol., 1996, 67: 140-149.

Collins et al., "Cultured human endothelial cells express platelet-derived growth factor B chain: cDNA cloning and structural analysis" Nature, 1985, 316: 748-750.

Dalla-Favera, "Chromosomal localization of the human homolog (c-sis) of the simian sarcoma virus onc gene" Science, 1982, Science, 218: 686-688.

DooLittle et al., "Simian sarcoma virus onc gene v-sis, is derived from the gene (or genes) encoding a platelet-derived growth factor" Science, 1982, 221: 275-277.

Fukui et al., "Isolation and characterization of Xenopus activin and follistatin" Devel. Biol., 1993, 159: 131-139.

Hee et al., "Do autologous growth factors enhance transforaminal lumbar interbody fusion?" Eur. Spine. J., 2003, 12(4): 400-407.

Helm et al., "Bone graft substitutes for the promotion of spinal arthrodesis," Neurosur. Foc., 2001, 10(4): 1-5.

Jones et al., "Isolation of Vgr-2, a novel member of the transforming growth factor- beta-related gene family" Mol. Endocrinol., 1992,6: 1961-1968.

Lioubavina-Hack et al., "Effect of Bio-Oss With or Without Platelet-Derived Growth Factor on Bone Formation by Guided Tissue Regeneration: A Pilot Study in Rats," Journal of Clinical Periodontology, 2005, 32(12): 1254-1260.

Lind et al, "Growth Factor Stimulation of Bone Healing," Acta orthopaedica Scandinavica Supplementum, 1998, 283: 2-37.

Lynch et al., "A New Era in Periodontal and Periimplant Regeneration: Use of Growth-Factor Enhanced Matrices Incorporating rhPDGF," Compendium of Continuing Education in Dentistry, 2006, 27(12): 672-678.

Marcopoulou et al., "Proliferative Effect of Growth Factors TGF-B1, PDGF-BB, and rhBMP-2 on Human Gingival Fibroblasts and Periodontal Ligament Cells," Journal of International Academy of Periodontology, 2003, 5(3): 63-70.

Mumford et al., "The Effects of Platelet Derived Growth Factor-BB on Periodontal Cells in In Vitro Wound Model," J. Periodontol., 2001, 72: 331-340.

Owen et al., "Simian sarcoma virus--transformed cells secrete a mitogen identical to platelet-derived growth factor" Science, 1984, 225: 54-56.

Park et al., "Periodontal Regeneration in Class III Furcation Defects of Beagle Dogs Using Guided Tissue Regenerative Therapy with Platelet-Derived Growth Factor" J. Periodontol., 1995, 66: 462-477.

Pfeilschifter et al., "Stimulation of Bone Matrix Apposition in Vitro by Local Growth Factors: A Comparison Between Insulin-Like Growth Factor I, Platelet Derived Growth Factor, and Transforming Growth Factor β," Endocrinology, 1990, 127(1): 69-75.

Rao et al., "Structure and Sequence of the Human C-Sis/Platelet-Derived Growth Factor 2" Proc. Natl. Acad. Sci. USA, 1986, 83: 2392-2396.

Robbins et al., "Structural and immunological similarities between simian sarcoma virus gene product(s) and human platelet-derived growth factor" Nature, 1983, 305: 605-608.

Sasai et al., "Xenopus chordin: a novel dorsalizing factor activated by organizer-specific homeobox genes," Cell, 1994, 79: 779-790.

Wang et al., "A Large Family of Putative Transmembrane Receptors Homologous to the Product of the Drosophila Tissue Polarity Gene frizzled" J. Biol.Chem., 1996, 271: 4468-4476.

Wikesjo et al., Repair of periodontal furcation defects in beagle dogs following reconstructive surgery including root surface demineralization with tetracycline hydrochloride and topical fibronectin application J. Clin. Periodontol., 1988, 15: 73-80.

Wikesjo et al., "Effects of subgingival irrigation on A. actinomycetemcomitans" J. Clin. Periodontol., 1989, 16:116-119.

* cited by examiner

PLATELET-DERIVED GROWTH FACTOR COMPOSITIONS AND METHODS OF USE THEREOF

CROSS REFERENCE TO RELATED APPLICATIONS

This application is a continuation-in-part of, and claims priority from, U.S. patent application Ser. No. 10/965,319, now abandoned, filed Oct. 14, 2004, which is incorporated herein by reference in its entirety.

FIELD OF THE INVENTION

This invention relates to the healing of bone and connective tissues.

BACKGROUND OF THE INVENTION

Growth factors are proteins that bind to receptors on a cell surface, with the primary result of activating cellular proliferation and/or differentiation. Many growth factors are quite versatile, stimulating cellular division in numerous different cell types; while others are specific to a particular cell-type. Examples of growth factors include platelet-derived growth factor (PDGF), insulin-like growth factors IGF-I and II), transforming growth factor beta (TGF-β), epidermal growth factor (EGF), and fibroblast growth factor (FGF). PDGF is a cationic, heat stable protein found in a variety of cell types, including the granules of circulating platelets, vascular smooth muscle cells, endothelial cells, macrophage, and keratinocytes, and is known to stimulate in vitro protein synthesis and collagen production by fibroblasts. It is also known to act as an in vitro mitogen and chemotactic agent for fibroblasts, smooth muscle cells, osteoblasts, and glial cells.

Recombinant human PDGF-BB (rhPDGF-BB) has been shown to stimulate wound healing and bone regeneration in both animals and humans. It is approved in both the United States and Europe for human use in topical applications to accelerate healing of chronic diabetic foot sores. Recombinant hPDGF-BB has also been shown to be effective either singly or in combination with other growth factors for improving periodontal regeneration, i.e., regrowth of bone, cementum, and ligament around teeth (see, e.g., U.S. Pat. No. 5,124,316, incorporated herein by reference).

SUMMARY OF THE INVENTION

We have now demonstrated that a low dose of rhPDGF (~0.1 to 1.0 mg/mL) promotes repair of bone, periodontium, ligament, and cartilage. A low amount of rhPDGF can be adsorbed to β-TCP, which can be implanted at the site of repair, such that the rhPDGF is released in vivo. Addition of rhPDGF to β-TCP has been shown to enhance osteoblast cell attachment and proliferation compared to untreated β-TCP.

In a first aspect, the invention features a method for promoting bone, periodontium, ligament, or cartilage growth in a mammal, e.g., a human, by administering an implant material containing platelet-derived growth factor (PDGF) at a concentration of less than about 1.0 mg/ml, such that the implant material promotes growth of the bone, periodontium, ligament, or cartilage. In an embodiment, the PDGF is administered in an amount of less than or equal to 0.3 mg/ml. In another embodiment, the PDGF is administered in an amount in the range of about 0.1 to about 1.0 mg/ml. In several embodiments, the PDGF is administered in an amount of between about 0.2 to about 0.75 mg/ml, about 0.25 to about 0.6 mg/ml, and about 0.25 to about 0.5 mg/ml. In an embodiment, the PDGF is administered in an amount of about 0.1 mg/ml, 0.3 mg/ml, or 1.0 mg/ml, preferably 0.3 mg/mL. In another embodiment, the PDGF is either partially or substantially purified. In yet a further embodiment, the PDGF is isolated or purified from other contaminants. In a further embodiment, the PDGF is released from the implant material upon administration at an average rate of 0.3 mg/day. In another embodiment, the PDGF is released from the implant material upon administration at an average rate of 300 μg/day. In still further embodiments, the PDGF is released from the implant material at an average rate of less than 100 μg/day, less than 50 μg/day, less than 10 μg/day, or less than 1 μg/day. Preferably, the PDGF is delivered over a few days, e.g., 1, 2, 5, 10, 15, 20, or 25 days, or up to 28 days or more.

A second aspect of the invention features a method for promoting bone, periodontium, ligament, or cartilage growth in a mammal, e.g., a human, by administering an implant material containing an amount of platelet-derived growth factor (PDGF) of less than about 1.0 mg/ml and a pharmaceutically acceptable carrier such that the implant material promotes the growth of the bone, periodontium, ligament, or cartilage, and allowing the bone, periodontium, ligament, or cartilage to grow. Preferably, the PDGF is equal to or less than about 0.3 mg/ml. In an embodiment, the PDGF is administered in a range of about 0.1 to 1.0 mg/ml. In other embodiments, the amount of PDGF is about 0.1 mg/ml, 0.3 mg/ml, or 1.0 mg/ml, preferably 0.3 mg/mL. In another embodiment, the PDGF is either partially or substantially purified. In yet a further embodiment, the PDGF is isolated or purified from other contaminants. Prior to administering the implant material to the mammal, the method can additionally include the step of producing a surgical flap of skin to expose the bone, periodontium, ligament, or cartilage, and following the administration step, replacing the flap. In yet another embodiment, after producing the surgical flap, but prior to administering the implant material to the bone, periodontium, ligament, or cartilage, the method can additionally include the step of planing the bone or periodontium to remove organic matter from the bone or periodontium. In yet another embodiment, the method promotes the growth of damaged or diseased bone, periodontium, ligament, or cartilage. In yet another embodiment, the method promotes the growth of bone in locations where new bone formation is required as a result of surgical interventions, such as, e.g., tooth extraction, ridge augmentation, esthetic grafting, and sinus lift.

A third aspect of the invention features an implant material for promoting the growth of bone, periodontium, ligament, or cartilage in a mammal, e.g., a human. The implant material includes a pharmaceutically acceptable carrier (e.g., a biocompatible binder, a bone substituting agent, a liquid, or a gel) and platelet-derived growth factor (PDGF), which is present at a concentration of less than about 1.0 mg/mL. Preferably, the PDGF is present in the implant material at a concentration equal to or less than about 0.3 mg/ml. In an embodiment, the PDGF is administered in a range of about 0.1 to 1.0 mg/ml. In other embodiments, the amount of PDGF is about 0.1 mg/ml, 0.3 mg/ml, or 1.0 mg/ml, preferably 0.3 mg/mL. In an embodiment, the pharmaceutically acceptable carrier of the implant material includes a scaffold or matrix consisting of a biocompatible binder (e.g., carboxymethylcellulose) or a bone substituting agent (β-TCP) that is capable of absorbing a solution that includes PDGF (e.g., a solution containing PDGF at a concentration in the range of about 0.1 mg/mL to about 1.0 mg/mL). In another embodiment, the pharmaceutically acceptable carrier is capable of absorbing an amount of the PDGF solution that is equal to at least about 25% of its own weight. In other embodiments, the pharmaceutically acceptable carrier is capable of absorbing an amount of the PDGF solution that is equal to at least about 50%, 75%, 100%, 200%, 250%, or 300% or its own weight. In an embodiment, the PDGF is absorbed by the pharmaceutically acceptable carrier of the implant material by soaking the pharmaceutically acceptable carrier in a solution containing PDGF. Preferably, the PDGF is present in the solution at a concentration of less than about 1.0 mg/mL. In another embodiment, the PDGF is present in the solution at a concentration equal to or less than about 0.3 mg/ml. In another embodiment, the PDGF is present in the solution at a concentration in the range of about 0.1 to 1.0 mg/ml. In yet other embodiments, the PDGF is present in the solution in an amount of about 0.1 mg/ml, 0.3 mg/ml, or 1.0 mg/ml, preferably 0.3 mg/mL. In another embodiment, the PDGF is either partially or substantially purified. In yet a further embodiment, the PDGF is isolated or purified from other contaminants.

A fourth aspect of the invention features a method for preparing an implant material for promoting growth of bone, periodontium, ligament, or cartilage in a mammal, e.g., a human. The method includes the step of combining partially purified or purified platelet-derived growth factor (PDGF) in an amount of less than about 1.0 mg/mL with a pharmaceutically acceptable carrier substance. Preferably, the PDGF is combined with a pharmaceutically acceptable carrier substance at a concentration equal to or less than about 0.3 mg/ml. In an embodiment, the PDGF is combined with a pharmaceutically acceptable carrier substance in an amount in the range of about 0.1 to 1.0 mg/ml. In other embodiments, PDGF is mixed in the amount of 0.1 mg/ml, 0.3 mg/ml, or 1.0 mg/ml. In another embodiment, PDGF is mixed in the amount of 0.3 mg/ml. In yet another embodiment, the PDGF is absorbed by the pharmaceutically acceptable carrier to produce the implant material.

A fifth aspect of the invention features a vial having platelet-derived growth factor (PDGF) at a concentration in the range of about 0.1 mg/mL to about 1.0 mg/mL in a pharmaceutically acceptable liquid. In an embodiment of this aspect of the invention, the liquid is sterile sodium acetate buffer. In another embodiment, the vial contains PDGF at a concentration of about 0.3 mg/mL. In yet another preferred embodiment, the PDGF is PDGF-BB. In yet other embodiments, the PDGF is stable in the sodium acetate buffer for at least about 12 months, preferably at least about 18 months, more preferably at least about 24 months, and most preferably at least about 36 months when stored at a temperature in the range of about 2° C. to 80° C.

A sixth aspect of the invention features an implant material that includes a porous calcium phosphate having adsorbed therein a liquid containing platelet-derived growth factor (PDGF) at a concentration in the range of about 0.1 mg/mL to about 1.0 mg/mL. In several embodiments, the concentration of PDGF is about 0.3 mg/mL, the calcium phosphate is selected from tricalcium phosphate, hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate, and the PDGF is provided in a sterile liquid, for example, sodium acetate buffer.

A seventh aspect of the invention features a method of preparing an implant material by saturating a calcium phosphate material in a sterile liquid that includes platelet-derived growth factor (PDGF) at a concentration in the range of about 0.1 mg/mL to about 1.0 mg/mL. In several embodiments, the concentration of PDGF is about 0.3 mg/mL, and the calcium phosphate is selected from tricalcium phosphate, hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate.

In an embodiment of all aspects of the invention, PDGF includes PDGF homo- and heterodimers, for example, PDGF-AA, PDGF-BB, PDGF-AB, PDGF-CC, and PDGF-DD, and combinations and derivatives thereof.

In an embodiment of all aspects of the invention, the pharmaceutically acceptable carrier substance of the implant material is or additionally includes one or more of the following: a biocompatible binder (e.g., a natural or synthetic polymer), a bone substituting agent, a liquid, and a gel. In another preferred embodiment, the implant material includes PDGF present in a pharmaceutically acceptable liquid carrier which is adsorbed by a pharmaceutically acceptable solid carrier.

In another embodiment of all aspects of the invention, the implant material is prepared by combining isolated, partially purified, substantially purified, or purified PDGF in an amount in the range of 0.1 to 1.0 mg/ml, more preferably 0.1 mg/ml, 0.3 mg/ml, or 1.0 mg/ml, most preferably 0.3 mg/ml, or even less than 0.1 mg/ml, with a pharmaceutically acceptable carrier substance, e.g., a biocompatible binder, such as a natural or synthetic polymer (e.g., collagen, polyglycolic acid, and polylactic acid), a bone substituting agent (e.g., a calcium phosphate (e.g., tricalcium phosphate or hydroxyapatite), calcium sulfate, or demineralized bone (e.g., demineralized freeze-dried cortical or cancellous bone), or a commercially available gel or liquid (i.e., a viscous or inert gel or liquid).

In several embodiments, the carrier substance of the implant material is, or additionally includes, one or more biocompatible binders. A biocompatible binder is an agent that produces or promotes cohesion between the combined substances. Non-limiting examples of suitable biocompatible binders include polymers selected from polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyglycolic acid, polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers and mixtures thereof. Additional binders include alginic acid, arabic gum, guar gum, xantham gum, gelatin, chitin, chitosan, chitosan acetate, chitosan lactate, chondroitin sulfate, N,O-carboxymethyl chitosan, a dextran (e.g., $\alpha$-cyclodextrin, $\beta$-cyclodextrin, $\gamma$-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and derivatives and mixtures thereof. In some embodiments, the biocompatible binder is water-soluble. A water-soluble binder dissolves from the implant material shortly after its implantation in vivo, thereby introducing macroporosity into the implant material. This macroporosity increases the osteoconductivity of the implant material by enhancing the access and, consequently, the remodeling activity of the osteoclasts and osteoblasts at the implant site.

The biocompatible binder may be added to the implant material in varying amounts and at a variety of stages during the preparation of the composition. Those of skill in the art will be able to determine the amount of binder and the method of inclusion required for a given application.

In an embodiment, the carrier substance is or includes a liquid selected from water, a buffer, and a cell culture medium. The liquid may be used in any pH range, but most often will be used in the range of pH 5.0 to pH 8.0. In an embodiment, the pH will be compatible with the prolonged stability and efficacy of the PDGF present in the implant material, or with the prolonged stability and efficacy of another desired biologically active agent. In most embodiments, the pH of the liquid will be in the range of pH 5.5 to pH 7.4. Suitable buffers include, but are not limited to, carbonates, phosphates (e.g., phosphate buffered saline), and organic buffers such as Tris, HEPES, and MOPS. Most often, the buffer will be selected for its biocompatibility with the host tissues and its compatibility with the biologically active agent. For most applications in which nucleic acids, peptides, or antibiotics are included in the implant material, a simple phosphate buffered saline will suffice.

In another embodiment of all aspects of the invention, the carrier substance of the implant material is, or additionally includes, one or more bone substituting agents. A bone substituting agent is one that can be used to permanently or temporarily replace bone. Following implantation, the bone substituting agent can be retained by the body or it can be resorbed by the body and replaced with bone. Exemplary bone substituting agent include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, or demineralized bone (e.g., demineralized freeze-dried cortical or cancellous bone)). In an embodiment, the carrier substance is bioresorbable. In another embodiment, the bone substituting agent is provided as a matrix of micron- or submicron-sized particles, e.g., nano-sized particles. The particles can be in the range of about 100 μm to about 5000 μm in size, or in the range of about 100 μm to about 3000 μm in size, more preferably in the range of about 200 μm to about 3000 μm, and most preferably in the range of about 250 μm to about 2000 μm, or the particles can be in the range of about 1 nm to about 1000 nm, preferably less than about 500 nm, and more preferably less than about 250 nm. In another embodiment, the bone substituting agent has a porous composition. Porosity of the composition is a desirable characteristic as it facilitates cell migration and infiltration into the composition so that the cells can secrete extracellular bone matrix. It also provides access for vascularization. Porosity also provides a high surface area for enhanced resorption and release of active substances, as well as increased cell-matrix interaction. Preferably, the composition has a porosity of greater than 40%, more preferably greater than 65%, and most preferably greater than 90%. The composition can be provided in a shape suitable for implantation (e.g., a sphere, a cylinder, or a block) or it can be sized and shaped prior to use. In a preferred embodiment, the bone substituting agent is a calcium phosphate (e.g., β-TCP).

The bone substituting agent can also be provided as a flowable, moldable paste or putty. Preferably, the bone substituting agent is a calcium phosphate paste that self-hardens to form a hardened calcium phosphate prior to or after implantation in vivo. The calcium phosphate component of the invention may be any biocompatible calcium phosphate material known in the art. The calcium phosphate material may be produced by any one of a variety of methods and using any suitable starting components. For example, the calcium phosphate material may include amorphous, apatitic calcium phosphate. Calcium phosphate material may be produced by solid-state acid-base reaction of crystalline calcium phosphate reactants to form crystalline hydroxyapatite solids. Other methods of making calcium phosphate materials are known in the art, some of which are described below.

The calcium phosphate material can be poorly crystalline apatitic (PCA) calcium phosphate or hydroxyapatite (HA). PCA material is described in application U.S. Pat. Nos. 5,650,176; 5,783,217; 6,027,742; 6,214,368; 6,287,341; 6,331,312; and 6,541,037, all of which are incorporated herein by reference. HA is described, for example, in U.S. Pat. No. Re. 33,221 and Re. 33,161. These patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905. This calcium phosphate material is produced by solid-state acid-base reaction of crystalline calcium phosphate reactants to form crystalline hydroxyapatite solids.

Crystalline HA materials (commonly referred to as dahllite) may be prepared such that they are flowable, moldable, and capable of hardening in situ (see U.S. Pat. No. 5,962,028). These HA materials (commonly referred to as carbonated hydroxyapatite) can be formed by combining the reactants with a non-aqueous liquid to provide a substantially uniform mixture, shaping the mixture as appropriate, and allowing the mixture to harden in the presence of water (e.g., before or after implantation). During hardening, the mixture crystallizes into a solid and essentially monolithic apatitic structure.

The reactants will generally consist of a phosphate source, e.g., phosphoric acid or phosphate salts, substantially free of water, an alkali earth metal, particularly calcium, source, optionally crystalline nuclei, particularly hydroxyapatite or calcium phosphate crystals, calcium carbonate, and a physiologically acceptable lubricant, such as any of the non-aqueous liquids described herein. The dry ingredients may be pre-prepared as a mixture and subsequently combined with the non-aqueous liquid ingredients under conditions where substantially uniform mixing occurs.

The calcium phosphate material is characterized by its biological resorbability, biocompatibility, and its minimal crystallinity. Its crystalline character is substantially the same as natural bone. Preferably, the calcium phosphate material hardens in less than five hours, and substantially hardens in about one to five hours, under physiological conditions. Preferably, the material is substantially hardened within about 10-30 minutes. The hardening rate under physiological conditions, may be varied according to the therapeutic need by modifying a few simple parameters as described in U.S. Pat. No. 6,027,742, which is incorporated herein by reference.

In an embodiment, the resulting bioresorbable calcium phosphate material will be "calcium deficient," with a calcium to phosphate molar ratio of less than about 1.6 as compared to the ideal stoichiometric value of approximately 1.67 for hydroxyapatite.

Desirable calcium phosphates are capable of hardening in a moist environment, at or around body temperature in less than 5 hours and preferably within 10-30 minutes. Desirable materials are those that, when implanted as a 1-5 g pellet, are at least 80% resorbed within one year. Preferably, the material can be fully resorbed.

In several embodiments of all aspects of the invention, the implant material additionally may include one or more biologically active agents. Biologically active agents that can be incorporated into the implant materials of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the implant materials of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and antihormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |
| | epirubicin | bleomycin sulfate (blenoxane) |
| | therarubicin | bleomycinic acid |
| | idarubicin | bleomycin A |
| | rubidazone | bleomycin B |
| | plicamycinp | mitomycin C |
| | porfiromycin | MEN-10755 (Menarini) |
| | cyanomorpholinodoxorubicin | GPX-100 (Gem Pharmaceuticals) |
| | mitoxantrone (novantrone) | |

TABLE 1-continued

| | | |
|---|---|---|
| Antimitotic agents | paclitaxel<br>docetaxel<br>colchicine<br>vinblastine<br>vincristine<br>vinorelbine<br>vindesine<br>dolastatin 10 (NCI)<br>rhizoxin (Fujisawa)<br>mivobulin (Warner-Lambert)<br>cemadotin (BASF)<br>RPR 109881A (Aventis)<br>TXD 258 (Aventis)<br>epothilone B (Novartis)<br>T 900607 (Tularik)<br>T 138067 (Tularik)<br>cryptophycin 52 (Eli Lilly)<br>vinflunine (Fabre)<br>auristatin PE (Teikoku Hormone)<br>BMS 247550 (BMS)<br>BMS 184476 (BMS)<br>BMS 188797 (BMS)<br>taxoprexin (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTAMedica)<br>ER-86526 (Eisai)<br>combretastatin A4 (BMS)<br>isohomohalichondrin-B (PharmaMar)<br>ZD 6126 (AstraZeneca)<br>PEG-paclitaxel (Enzon)<br>AZ10992 (Asahi)<br>IDN-5109 (Indena)<br>AVLB (Prescient NeuroPharma)<br>azaepothilone B (BMS)<br>BNP-7787 (BioNumerik)<br>CA-4 prodrug (OXiGENE)<br>dolastatin-10 (NIH)<br>CA-4 (OXiGENE) |
| Aromatase inhibitors | aminoglutethimide<br>letrozole<br>anastrazole<br>formestane | exemestane<br>atamestane (BioMedicines)<br>YM-511 (Yamanouchi) |
| Thymidylate synthase inhibitors | pemetrexed (Eli Lilly)<br>ZD-9331 (BTG) | nolatrexed (Eximias)<br>CoFactor ™ (BioKeys) |
| DNA antagonists | trabectedin (PharmaMar)<br>glufosfamide (Baxter International)<br>albumin + 32P (Isotope Solutions)<br>thymectacin (NewBiotics)<br>edotreotide (Novartis) | mafosfamide (Baxter International)<br>apaziquone (Spectrum Pharmaceuticals)<br>O6 benzyl guanine (Paligent) |
| Farnesyltransferase inhibitors | arglabin (NuOncology Labs)<br>lonafarnib (Schering-Plough)<br>BAY-43-9006 (Bayer) | tipifarnib (Johnson & Johnson)<br>perillyl alcohol (DOR BioPharma) |
| Pump inhibitors | CBT-1 (CBA Pharma)<br>tariquidar (Xenova)<br>MS-209 (Schering AG) | zosuquidar trihydrochloride (Eli Lilly)<br>biricodar dicitrate (Vertex) |
| Histone acetyltransferase inhibitors | tacedinaline (Pfizer)<br>SAHA (Aton Pharma)<br>MS-275 (Schering AG) | pivaloyloxymethyl butyrate (Titan)<br>depsipeptide (Fujisawa) |
| Metalloproteinase inhibitors | Neovastat (Aeterna Laboratories)<br>marimastat (British Biotech) | CMT-3 (CollaGenex)<br>BMS-275291 (Celltech) |
| Ribonucleoside reductase inhibitors | gallium maltolate (Titan)<br>triapine (Vion) | tezacitabine (Aventis)<br>didox (Molecules for Health) |
| TNF alpha agonists/antagonists | virulizin (Lorus Therapeutics)<br>CDC-394 (Celgene)<br>infliximab (Centocor, Inc.)<br>adalimumab (Abbott Laboratories) | revimid (Celgene)<br>entanercept (Immunex Corp.) |
| Endothelin A receptor antagonist | atrasentan (Abbott)<br>ZD-4054 (AstraZeneca) | YM-598 (Yamanouchi) |
| Retinoic acid receptor agonists | fenretinide (Johnson & Johnson)<br>LGD-1550 (Ligand) | alitretinoin (Ligand) |
| Immuno-modulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (GemVax) | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen) |
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate; fluoxymesterone<br>methyltestosterone<br>diethylstilbestrol<br>megestrol | prednisone<br>methylprednisolone<br>prednisolone<br>aminoglutethimide<br>leuprolide<br>goserelin<br>leuporelin<br>bicalutamide<br>flutamide<br>octreotide<br>nilutamide<br>mitotane |

TABLE 1-continued

| | | |
|---|---|---|
| | tamoxifen | P-04 (Novogen) |
| | toremofine | 2-methoxyestradiol (EntreMed) |
| | dexamethasone | arzoxifene (Eli Lilly) |
| Photodynamic agents | talaporfin (Light Sciences) | Pd-bacteriopheophorbide (Yeda) |
| | Theralux (Theratechnologies) | lutetium texaphyrin (Pharmacyclics) |
| | motexafin gadolinium (Pharmacyclics) | hypericin |
| Tyrosine Kinase Inhibitors | imatinib (Novartis) | kahalide F (PharmaMar) |
| | leflunomide (Sugen/Pharmacia) | CEP-701 (Cephalon) |
| | ZD1839 (AstraZeneca) | CEP-751 (Cephalon) |
| | erlotinib (Oncogene Science) | MLN518 (Millenium) |
| | canertinib (Pfizer) | PKC412 (Novartis) |
| | squalamine (Genaera) | phenoxodiol () |
| | SU5416 (Pharmacia) | trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramisole, 10-(alpha-diethylaminopropionyl)-phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, nonsteroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenylbutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, nor-binaltorphimine, buprenorphine, chlornaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Growth factors are factors whose continued presence improves the viability or longevity of a cell. Trophic factors include, without limitation, neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor (IGF, e.g., IGF-I or IGF-II), glial derived growth neurotrophic factor, ciliary neurotrophic factor, nerve growth factor, bone growth/cartilage-inducing factor (alpha and beta), bone morphogenetic proteins (BMPs), interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, transforming growth factors (beta), including beta-1, beta-2, beta-3, transforming growth factors (alpha), inhibin, and activin; and bone morphogenetic proteins such as OP-1, BMP-2 and BMP-7.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The biologically active agent is also desirably selected from the family of proteins known as the transforming growth factors-beta (TGF-β) superfamily of proteins, which includes the activins, inhibins, and bone morphogenetic proteins (BMPs). In an embodiment, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins which may be useful as the active agent in the calcium phosphate compositions of the invention include Vgr-2, Jones et al., *Mol. Endocrinol.* 6:1961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention may be BIP, disclosed in WO94/01557; HP00269, disclosed in JP Publication number: 7-250688; and MP52, disclosed in PCT application WO93/16099. The disclosures of all of the above applications are incorporated herein by reference. A subset of BMPs which can be used in the invention include BMP-2, BMP-4, BMP-5, BMP-6, BMP-7, BMP-10, BMP-12, BMP-13, BMP-14, and MP52. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, LIM protein, osteogenin, or demineralized bone matrix (DBM), among others.

The biologically active agent may be synthesized chemically, recombinantly produced, or purified from a source in which the biologically active agent is naturally found. The active agent, if a TGF-β, such as a BMP or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is incorporated herein by reference.

Additional biologically active agents include the Hedgehog, Frazzled, Chordin, Noggin, Cerberus, and Follistatin proteins. These families of proteins are generally described in Sasai et al., Cell 79:779-790 (1994) (Chordin); PCT Patent Publication WO94/05800 (Noggin); and Fukui et al., *Devel. Biol.* 159:131 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., *J. Biol. Chem.* 271:4468-4476 (1996). The active agent may also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are incorporated by reference herein.

The amount of the biologically active protein, e.g., an osteogenic protein, that is effective to stimulate a desired activity, e.g., increased osteogenic activity of present or infiltrating progenitor or other cells, will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Standard protocols and regimens for delivery of the above-listed agents are known in the art. Biologically active agents are introduced into the implant material in amounts that allow delivery of an appropriate dosage of the agent to the implant site. In most cases, dosages are determined using guidelines known to practitioners and applicable to the particular agent in question. The exemplary amount of biologically active agent to be included in the implant material of the invention is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent.

In an embodiment of all aspects of the invention, the composition can additionally contain autologous bone marrow or autologous platelet extracts.

In another embodiment of all of the above aspects, the PDGF and/or other growth factors can be obtained from natural sources, (e.g., platelets), or more preferably, produced by recombinant DNA technology. When obtained from natural sources, the PDGF and/or other growth factors can be obtained from a biological fluid. A biological fluid includes any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. The biological fluid may have been treated to remove some of the leukocytes before being processed according to the invention. As used herein, blood product or biological fluid refers to the components described above, and to similar blood products or biological fluids obtained by other means and with similar properties. In an embodiment, the PDGF is obtained from platelet-rich plasma (PRP). The preparation of PRP is described in, e.g., U.S. Pat. Nos. 6,649,072, 6,641,552, 6,613,566, 6,592,507, 6,558,307, 6,398,972, and 5,599,558, which are incorporated herein by reference.

In an embodiment of all aspects of the invention, the implant material delivers PDGF at the implant site for a duration of time greater than at least 1 day. In several embodiments, the implant material delivers PDGF at the implant site for at least 7, 14, 21, or 28 days. Preferably, the implant material delivers PDGF at the implant site for a time between about 1 day and 7, 14, 21, or 28 days. In another embodiment, the implant material delivers PDGF at the implant site for a time greater than about 1 day, but less than about 14 days.

By "bioresorbable" is meant the ability of the implant material to be resorbed or remodeled in vivo. The resorption process involves degradation and elimination of the original implant material through the action of body fluids, enzymes or cells. The resorbed materials may be used by the host in the formation of new tissue, or it may be otherwise re-utilized by the host, or it may be excreted.

By "differentiation factor" is meant a polypeptide, including a chain of at least 6 amino acids, which stimulates differentiation of one or more target cells into cells with cartilage or bone forming potential.

By "nanometer-sized particle" is meant a submicron-sized particle, generally defined as a particle below 1000 nanometers. A nanometer-sized particle is a solid particle material that is in an intermediate state between molecular and macron substances. A nanometer is defined as one billionth of a meter (1 nanometer=$10^9$ m). Nanometer material is known as the powder, fiber, film, or block having nanoscale size.

By "periodontium" is meant the tissues that surround and support the teeth. The periodontium supports, protects, and provides nourishment to the teeth. The periodontium consists of bone, cementum, alveolar process of the maxillae and mandible, periodontal ligament, and gingiva. Cementum is a thin, calcified layer of tissue that completely covers the dentin of the tooth root. Cementum is formed during the development of the root and throughout the life of the tooth and functions as an area of attachment for the periodontal ligament fibers. The alveolar process is the bony portion of the maxilla and mandible where the teeth are embedded and in which the tooth roots are supported. The alveolar socket is the cavity within the alveolar process in which the root of the tooth is held by the periodontal ligament. The bone that divides one socket from another is called the interdental septum. When multirooted teeth are present, the bone is called the interradicular septum. The alveolar process includes the cortical plate, alveolar crest, trabecular bone, and the alveolar bone proper.

By "promoting growth" is meant the healing of bone, periodontium, ligament, or cartilage, and regeneration of such tissues and structures. Preferably, the bone, periodontium, ligament, or cartilage is damaged or wounded and requires regeneration or healing.

By "promoting periodontium growth" is meant regeneration or healing of the supporting tissues of a tooth including alveolar bone, cementum, and interposed periodontal ligament, which have been damaged by disease or trauma.

By "purified" is meant a growth or differentiation factor, e.g., PDGF, which, prior to mixing with a carrier substance, is 95% or greater by weight, i.e., the factor is substantially free of other proteins, lipids, and carbohydrates with which it is naturally associated. The term "substantially purified" refers to a lesser purity of factor, having, for example, only 5%-95% by weight of the factor, preferably 65-95%. A purified protein preparation will generally yield a single major band on a polyacrylamide gel. Most preferably, the purified factor used in implant materials of the invention is pure as judged by amino-terminal amino acid sequence analysis. The term "partially purified" refers to PDGF that is provided in the context of PRP, PPP, FFP, or any other blood product that requires collection and separation, e.g., by centrifugation, to produce.

By way of example, a solution having ~1.0 mg/mL of PDGF, when ~50% pure, constitutes ~2.0 mg/mL of total protein.

The implant materials of this invention aid in regeneration of periodontium, at least in part, by promoting the growth of connective tissue, bone, and cementum. The implant materials can be prepared so that they directly promote the growth and differentiation of cells that produce connective tissue, bone, and cementum. Alternatively, the implant materials can be prepared so that they act indirectly by, e.g., attracting cells that are necessary for promoting the growth of connective tissue, bone, and cementum. Regeneration using a composition of this invention is a more effective treatment of periodontal diseases or bone wounds than that achieved using systemic antibiotics or surgical debridement alone.

The PDGF, polypeptide growth factors, and differentiation factors may be obtained from human tissues or cells, e.g., platelets, by solid phase peptide synthesis, or by recombinant DNA technology. Thus, by the term "polypeptide growth factor" or "differentiation factor," we mean tissue or cell-derived, recombinant, or synthesized materials. If the factor is a dimer, e.g., PDGF, the recombinant factor can be a recombinant heterodimer, made by inserting into cultured prokaryotic or eukaryotic cells DNA sequences encoding both subunits of the factor, and then allowing the translated subunits to be processed by the cells to form a heterodimer (e.g., PDGF-AB). Alternatively, DNA encoding just one of the subunits (e.g., PDGF B-chain or A-chain) can be inserted into cells, which then are cultured to produce the homodimeric factor (e.g., PDGF-BB or PDGF-AA homodimers). PDGF for use in the methods of the invention includes PDGF homo- and heterodimers, for example, PDGF-AA, PDGF-BB, PDGF-AB, PDGF-CC, and PDGF-DD, and combinations and derivatives thereof.

The concentration of PDGF or other growth factors of the invention can be determined by using, e.g., an enzyme-linked immunoassay, as described in, e.g., U.S. Pat. Nos. 6,221,625, 5,747,273, and 5,290,708, incorporated herein by reference, or any other assay known in the art for determining protein concentration. When provided herein, the molar concentration of PDGF is determined based on the molecular weight of PDGF dimer (e.g., PDGF-BB; MW=approximately 25 kDa).

The methods and implant materials of the invention can be used to heal bony wounds of mammals, e.g., fractures, implant recipient sites, and sites of periodontal disease. The implant materials promote connective tissue growth and repair and enhance bone formation compared to natural healing (i.e., no exogenous agents added) or healing supplemented by addition of systemic antibiotics. Unlike natural healing, conventional surgical therapy, or antibiotics, the implant materials of the invention prompt increased bone, connective tissue (e.g., cartilage and ligament), and cementum formation when applied to damaged or diseased tissues or to periodontal disease affected sites. The restoration of these tissues leads to an improved prognosis for the affected areas. The ability of these factors to stimulate new bone formation also makes it applicable for treating bony defects caused by other types of infection or surgical or accidental trauma.

Other features and advantages of the invention will be apparent from the following description of the embodiments thereof, and from the claims.

BRIEF DESCRIPTION OF THE DRAWINGS

FIG. 1A is a photomicrograph showing the effect of surgery alone on bone formation. FIG. 1B is a photomicrograph showing the effect of β-TCP alone on bone formation. FIG. 1C is a photomicrograph showing the effect of β-TCP+0.3 mg/mL PDGF on bone formation. FIG. 1D is a photomicrograph showing the effect of β-TCP+1.0 mg/mL PDGF on bone formation. FIG. 1E is a photomicrograph showing the effect of demineralized freeze dried bone allograft (DFDBA) alone on bone formation. FIG. 1F is a photomicrograph showing the effect of demineralized freeze dried bone allograft (DFDBA)+0.3 mg/mL PDGF on bone formation. FIG. 1G is a photomicrograph showing the effect of demineralized freeze dried bone allograft (DFDBA)+1.0 mg/mL on bone formation.

FIG. 2A is a photomicrograph showing the effect of β-TCP alone on bone formation. FIG. 2B is a photomicrograph showing the effect of β-TCP+0.3 mg/mL PDGF on bone formation. FIG. 2C is a photomicrograph showing the effect of β-TCP+1.0 mg/mL PDGF on bone formation.

DETAILED DESCRIPTION

Figure 1:
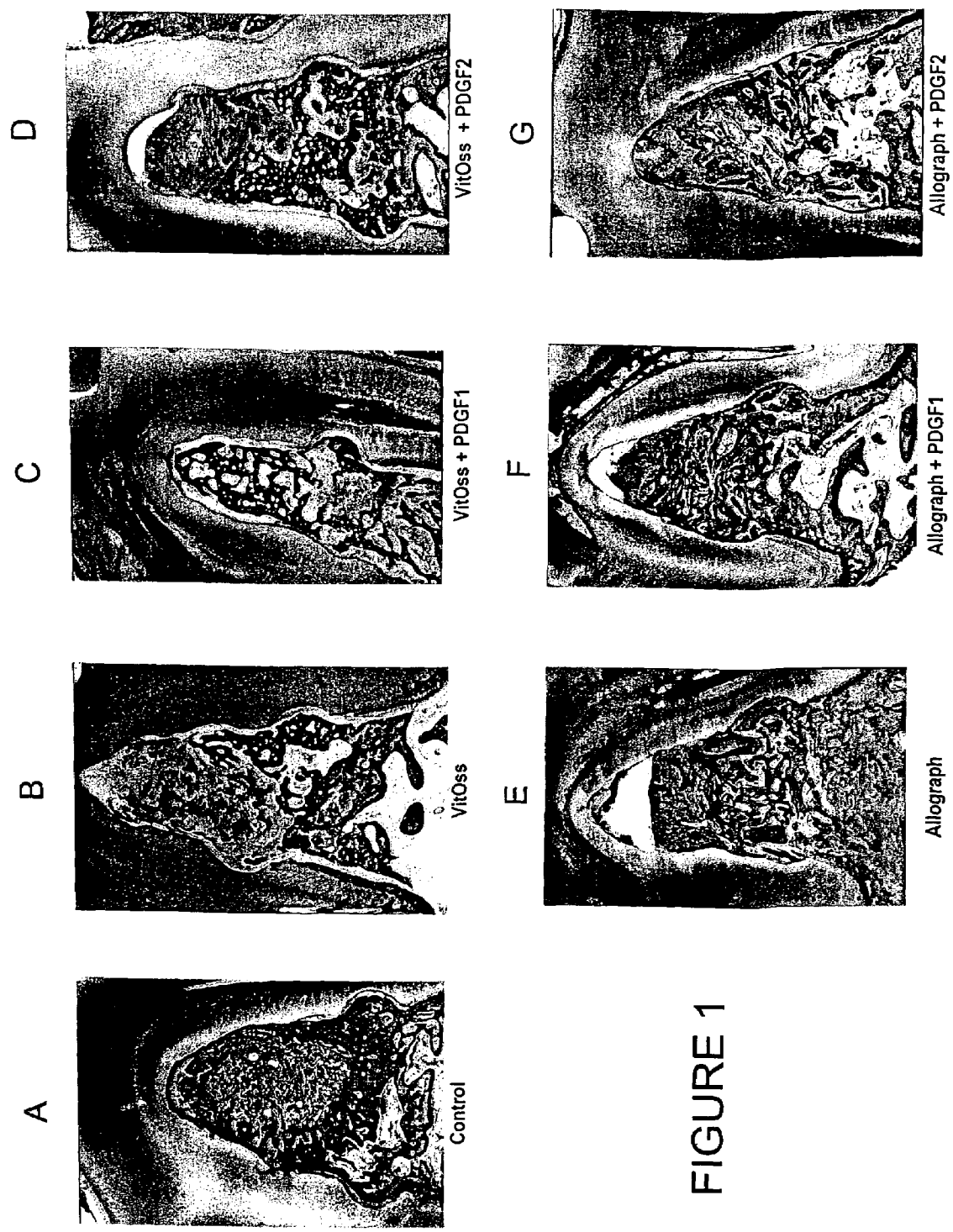
FIGS. 1A-1G are photomicrographs showing the effect on bone formation 8 weeks following treatment.

We now describe several embodiments of the invention. Two examples demonstrating the use of PDGF as a bone and periodontum healing agent are presented below.

EXAMPLES

Example I

Preparation of PDGF

Osseous wounds, e.g., following periodontal disease or trauma, are treated and periodontium, including bone, cementum, and connective tissue, are regenerated, according to the invention by combining partially purified or purified PDGF with any of the pharmaceutically acceptable carrier substances described above. Purified PDGF can be obtained from a recombinant source or from human platelets. Commercially available recombinant PDGF can be obtained from R&D Systems Inc. (Minneapolis, Minn.), BD Biosciences (San Jose, Calif.), and Chemicon, International (Temecula, Calif.). Partially purified and purified PDGF can also be prepared as follows:

Five hundred to 1000 units of washed human platelet pellets are suspended in 1M NaCl (2 ml per platelet unit) and heated at 100° C. for 15 minutes. The supernatant is then separated by centrifugation and the precipitate extracted twice with the 1 m NaCl.

The extracts are combined and dialyzed against 0.08M NaCl/0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl/0.01M sodium phosphate buffer (pH 7.4), and eluted with 1M NaCl while 10 ml fractions are collected.

Active fractions are pooled and dialyzed against 0.3M NaCl/0.01M sodium phosphate buffer (pH 7.4), centrifuged, and passed at 4° C. through a 2.5×25 cm column of blue sepharose (Pharmacia) equilibrated with 0.3M NaCl/0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl/0.01M sodium phosphate buffer (pH 7.4) and passed through a 1.2× 40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1M acetic acid. The PDGF is then eluted with 1M acetic acid while 2 mL fractions are collected.

Each active fraction containing 100 to 200 mg of protein is lyophilized, dissolved in 100 mL of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF Made by Recombinant DNA Technology can be Prepared as Follows:

Platelet-derived growth factor (PDGF) derived from human platelets contains two polypeptide sequences (PDGF-B and PDGF-A polypeptides; Antoniades, H. N. and Hunkapiller, M., *Science* 220:963-965, 1983). PDGF-B is encoded by a gene localized on chromosome 7 (Betsholtz, C. et al., *Nature* 320:695-699), and PDGF-A is encoded by the sis oncogene (Doolittle, R. et al., *Science* 221:275-277, 1983) localized on chromosome 22 (Dalla-Favera, R., *Science* 218: 686-688, 1982). The sis gene encodes the transforming protein of the Simian Sarcoma Virus (SSV) which is closely related to PDGF-2 polypeptide. The human cellular c-sis also encodes the PDGF-A chain (Rao, C. D. et al., *Proc. Natl. Acad. Sci. USA* 83:2392-2396, 1986). Because the two polypeptide chains of PDGF are coded by two different genes localized in separate chromosomes, the possibility exists that human PDGF consists of a disulfide-linked heterodimer of PDGF-B and PDGF-A, or a mixture of the two homodimers (PDGF-BB homodimer and PDGF-AA homodimer), or a mixture of the heterodimer and the two homodimers.

Mammalian cells in culture infected with the Simian Sarcoma Virus, which contains the gene encoding the PDGF-A chain, were shown to synthesize the PDGF-A polypeptide and to process it into a disulfide-linked homodimer (Robbins et al., *Nature* 305:605-608, 1983). In addition, the PDGF-A homodimer reacts with antisera raised against human PDGF. Furthermore, the functional properties of the secreted PDGF-A homodimer are similar to those of platelet-derived PDGF in that it stimulates DNA synthesis in cultured fibroblasts, it induces phosphorylation at the tyrosine residue of a 185 kD cell membrane protein, and it is capable of competing with human ($^{125}$I)-PDGF for binding to specific cell surface PDGF receptors (Owen, A. et al., *Science* 225:54-56, 1984). Similar properties were shown for the sis/PDGF-A gene product derived from cultured normal human cells (for example, human arterial endothelial cells), or from human malignant cells expressing the sis/PDGF-2 gene (Antoniades, H. et al., *Cancer Cells* 3:145-151, 1985).

The recombinant PDGF-B homodimer is obtained by the introduction of cDNA clones of α-sis/PDGF-B gene into mouse cells using an expression vector. The c-sis/PDGF-B clone used for the expression was obtained from normal human cultured endothelial cells (Collins, T., et al., *Nature* 216:748-750, 1985).

Use of PDGF

PDGF alone or in combination with other growth factors is useful for promoting bone healing, bone growth and regeneration or healing of the supporting structures of teeth injured by trauma or disease. It is also useful for promoting healing of a site of extraction of a tooth, for mandibular ridge augmentation, or at tooth implant sites. Bone healing would also be enhanced at sites of bone fracture or in infected areas, e.g., osteomyelitis, or at tumor sites. PDGF is also useful for promoting growth and healing of a ligament, e.g., the periodontal ligament, and of cementum.

In use, the PDGF or other growth or differentiation factor is applied directly to the area needing healing or regeneration. Generally, it is applied in a resorbable or non-resorbable carrier as a liquid or solid, and the site then covered with a bandage or nearby tissue. An amount sufficient to promote bone growth is generally between 500 ng and 5 mg for a 1 cm$^2$ area, but the upper limit is really 1 mg for a 1 cm$^2$ area, with a preferred amount of PDGF applied being 0.3 mg/mL.

Example II

Periodontal Regeneration with rhPDGF-BB Treated Osteoconductive Scaffolds

The effectiveness of PDGF in promoting periodontium and bone growth is demonstrated by the following study.

In Vivo Dog Study

The beagle dog is the most widely used animal model for testing putative periodontal regeneration materials and procedures (Wikesjo et al., *J. Clin. Periodontol.* 15:73-78, 1988; Wikesjo et al., *J. Clin. Periodontol.* 16:116-119, 1999; Cho et al., *J. Periodontol.* 66:522-530, 1995; Giannobile et al., *J. Periodontol.* 69:129-137, 1998; and Clergeau et al., *J. Periodontol.* 67:140-149, 1996). Plaque and calculus accumulation can induce gingival inflammation that may lead to marginal bone loss and the etiology of periodontitis in dogs and humans can be compared. In naturally occurring disease, however, there is a lack of uniformity between defects. Additionally, as more attention has been given to oral health in canine breeder colonies, it has become impractical to obtain animals with natural periodontal disease. Therefore, the surgically-induced horizontal Class III furcation model has become one of the most commonly used models to investigate periodontal healing and regeneration.

Beagle dogs with horizontal Class III furcation defects were treated using PDGF compositions of the invention. Fifteen adult beagle dogs contributed 60 treated defects. Forty-two defects were biopsied two months after treatment and fifteen defects were biopsied four months after treatment Defect Preparation The "critical-size" periodontal defect model as described by numerous investigators was utilized (see, e.g., Wikesjo, 1988 and 1999, supra; Giannobile, supra, Cho, supra, and Park et al., *J. Periodontol.* 66:462-477, 1995). Both mandibular quadrants in 16 male beagle dogs (2-3 years old) without general and oral health problems were used. One month prior to dosing, the animals were sedated with a subcutaneous injection of atropine (0.02 mg/kg) and acepromazine (0.2 mg/kg) approximately 30 minutes prior to being anesthetized with an IV injection of pentobarbital sodium (25 mg/kg). Following local infiltration of the surgical area with Lidocaine HCl plus epinephrine 1:100,000, full thickness mucoperiosteal flaps were reflected and the first and third premolars (P1 and P3) were extracted. Additionally, the mesial portion of the crown of the 1st molar was resected.

Alveolar bone was then removed around the entire circumference of P2 and P4, including the furcation areas using chisels and water-cooled carbide and diamond burs. Horizontal bone defects were created such that there was a distance of 5 mm from the fornix of the furcation to the crest of the bone. The defects were approximately 1 cm wide, depending on the width of the tooth. The roots of all experimental teeth were planed with curettes and ultrasonic instruments and instrumented with a tapered diamond bur to remove cementum. After the standardized bone defects were created the gingival flaps were sutured to achieve primary closure. The animals were fed a soft diet and received daily chlorhexidine rinses for the duration of the study.

Application of Graft Material

The periodontal defects of P2 and P4 in each mandibular quadrant of the 15 animals were randomized prior to treatment using sealed envelopes. About four weeks after defect preparation, animals were re-anesthetized as described above and full thickness flaps were reflected in both mandibular quadrants. A notch was placed in the tooth root surfaces at the residual osseous crest using a ½ round bur to serve as a future histologic reference point. The sites were irrigated with sterile saline and the roots were treated with citric acid as described previously for the purpose of decontamination and removal of the smear layer (See, e.g., Cho, supra, and Park, supra). During this period an amount of β-TCP or DFDBA sufficient to fill the periodontal defect was saturated with a solution of rhPDGF-BB solution (0.3 or 1.0 mg/ml) and the rhPDGF-BB/graft mixture was allowed to sit on the sterile surgical stand for about ten minutes. The rhPDGF-BB saturated graft was then packed into the defect with gentle pressure to the ideal level of osseous regeneration.

After implantation of the graft material, the mucoperiosteal flaps were sutured approximately level to the cementoenamel junction (CEJ) using interproximal, interrupted 4.0 expanded polytetrafluoroethylene (ePTFE) sutures. Following suturing of the flaps chlorhexidine gluconate gel was gently placed around the teeth and gingivae.

Treatment and Control Groups

Defects received either:

1. β-TCP
2. β-TCP plus rhPDGF-BB (0.3 mg/ml rhPDGF-BB)
3. β-TCP plus rhPDGF-BB (1.0 mg/ml rhPDGF-BB)
4. Dog DFDBA
5. Dog DFDBA plus rhPDGF-BB (0.3 mg/ml rhPDGF-BB)
6. Dog DFDBA plus rhPDGF-BB (1.0 mg/ml rhPDGF-BB)
7. Sham surgery (treated by open flap debridement only, no graft)

Six defects per treatment group were biopsied at two months (42 total sites). In addition, five defects in treatment groups 1, 2, and 3 were biopsied at four months (15 total sites).

TABLE 2

Experimental design

| GROUP No. | No. OF TEST SITES | TREATMENT | TIME POINTS |
|---|---|---|---|
| 1 | 11 | β-TCP alone | 8 & 16 weeks<br>n = 6 for 8 wk<br>n = 5 for 16 wk |
| 2 | 11 | β-TCP + 0.3 mg/ml rhPDGF-BB | 8 & 16 weeks<br>n = 6 for 8 wk<br>n = 5 for 16 wk |
| 3 | 11 | β-TCP + 1.0 mg/ml rhPDGF-BB | 8 & 16 weeks<br>n = 6 for 8 wk<br>n = 5 for 16 wk |
| 4 | 6 | DFDBA alone | 8 weeks |
| 5 | 6 | DFDBA + 0.3 mg/ml rhPDGF-BB | 8 weeks |
| 6 | 6 | DFDBA + 1.0 mg/ml rhPDGF-BB | 8 weeks |
| 7 | 6 | Surgery, no graft | 8 weeks |

Accordingly, at 8 weeks there are 7 groups divided among 42 sites in 11 dogs. At 16 weeks, there are 3 groups divided among 15 sites in 4 dogs (one dog received two treatment surgeries staggered eight weeks apart and thus contributed two sites to each the 8 and 16 week time points).

Post-Surgical Treatment

The surgical sites were protected by feeding the dogs a soft diet during the first 4 weeks post-operative. To insure optimal healing, systemic antibiotic treatment with penicillin G benzathine was provided for the first two weeks and plaque control was maintained by daily irrigation with 2% chlorhexidine gluconate throughout the experiment. Sutures were removed after 3 weeks.

Data Collection

Rationale for Data Collection Points

The eight week time point was chosen because this is the most common time point reported for this model in the literature and therefore there are substantial historical data. For example, Wikesjo et al., supra, and Giannobile et al., supra, also chose 8 weeks to assess the regenerative effects of BMP-2 and OP-1, respectively, in the same model. Additionally, Park et al., supra, evaluated the effect or rhPDGF-BB applied directly to the conditioned root surface with and without GTR membranes in the beagle dog model at 8 weeks. These studies, strongly suggest that the 8 week period should be optimal for illustrating potential significant effects among the various treatment modalities.

The sixteen week time point was chosen to assess longterm effects of growth factor treatment. Previous studies (Park et al., supra) suggest that by this time there is substantial spontaneous healing of the osseous defects. Nevertheless, it is possible to assess whether rhPDGF-BB treatment leads to any unusual or abnormal tissue response, such as altered bone remodeling, tumorgenesis or root resorption.

Biopsies and Treatment Assessments

At the time of biopsy, the animals were perfused with 4% paraformaldehyde and sacrificed. The mandibles were then removed and placed in fixative. Periapical radiographs were taken and the treated sites were cut into individual blocks using a diamond saw. The coded (blinded) blocks were wrapped in gauze, immersed in a solution of 4% formaldehyde, processed, and analyzed.

During processing the biopsies were dehydrated in ethanol and infiltrated and embedded in methylmethacrylate. Undecalcified sections of approximately 300 μm in thickness were obtained using a low speed diamond saw with coolant. The sections were glued onto opalescent acrylic glass, ground to a final thickness of approximately 80 μm, and stained with toludine blue and basic fuchsin. Step serial sections were obtained in a mesiodistal plane.

Histomorphometric analyses were performed on the masked slides. The following parameters were assessed:

1. Length of Complete New Attachment Apparatus (CNAA): Periodontal regeneration measured as the distance between the coronal level of the old bone and the coronal level of the new bone, including only that new bone adjacent to new cementum with functionally oriented periodontal ligament between the new bone and new cementum.

2. New Bone Fill (NB): Measured as the cross-sectional area of new bone formed within the furcation.

3. Connective Tissue fill (CT): Measured as the area within the furcation occupied by gingival connective tissue.

4. Void (VO): The area of recession where there is an absence of tissue.

Results

A. Clinical Observations

Clinically, all sites healed well. There was an impression that the sites treated with rhPDGF-BB healed more quickly, as indicated by the presence of firm, pink gingivae within one week post-operatively. There were no adverse events experienced in any treatment group as assessed by visual inspection of the treated sites. There appeared to be increased gingival recession in groups that received β-TCP or DFDBA alone.

B. Radiographic Observations

Radiographically, there was evidence of increased bone formation at two months as judged by increased radiopacity in Groups 2, 3 (β-TCP+rhPDGF-BB 0.3 and 1.0 mg/ml, respectively) and 6 (DFDBA+rhPDGF-BB 1.0 mg/ml) compared to the other groups (FIGS. 1A-G). At four months, there was evidence of increased bone formation in all groups compared to the two month time point. There was no radiographic evidence of any abnormal bone remodeling, root resorption, or ankylosis in any group.

TABLE 3

Radiographic results. Rank order.

| QUALITATIVE ASSESSMENT OF BONE FILL AT 8 WKS* | TREATMENT |
|---|---|
| 6 | β-TCP alone |
| 1 | β-TCP + 0.3 mg/ml rhPDGF |
| 2 | β-TCP + 1.0 mg/ml rhPDGF |
| 7 | DFDBA alone |
| 5 | DFDBA + 0.3 mg/ml rhPDGF |
| 3 | DFDBA + 1.0 mg/ml rhPDGF |
| 4 | Surgery, no graft |

*1 = most fill; 7 = least fill

C. Histomorphometric Analyses:

Histomorphometric assessment of the length of new cementum, new bone, and new periodontal ligament (CNAA) as well as new bone fill, connective tissue fill, and void space were evaluated and are expressed as percentages. In the case of CNAA, values for each test group represent the CNAA measurements (length in mm)/total available CNAA length (in mm)×100%. Bone fill, connective tissue fill and void space were evaluated and are expressed as percentages of the total furcation defect area.

One-way analysis of variance (ANOVA) was used to test for overall differences among treatment groups, and pairwise comparisons were made using the student's t-test. Significant differences between groups were found upon analyses of the coded slides. Table 4 shows the results at two months.

TABLE 4

| | | Two month histometric analyses | | | |
|---|---|---|---|---|---|
| GROUP No. | TREATMENT | % CNAA PERIODONTAL REGENERATION | % BONE FILL | % CONNECTIVE TISSUE FILL | % VOID |
| 1 | β-TCP alone | 37.0 ± 22.8** | 28.0 ± 29.5 | 36.0 ± 21.5 | 12.0 ± 17.9 |
| 2 | β-TCP + 0.3 mg/ml rhPDGF | 59.0 ± 19.1*,† | 84.0 ± 35.8†,‡ | 0.0 ± 0.0 | 8.0 ± 17.9 |
| 3 | β-TCP + 1.0 mg/ml rhPDGF | 46.0 ± 12.3* | 74.2 ± 31.7‡ | 0.0 ± 0.0 | 0.0 ± 0.0 |
| 4 | DFDBA alone | 13.4 ± 12.0 | 6.0 ± 8.9 | 26.0 ± 19.5 | 30.0 ± 27.4 |
| 5 | DFDBA + 0.3 mg/ml rhPDGF | 21.5 ± 13.3 | 20.0 ± 18.7 | 36.0 ± 13.4 | 18.0 ± 21.7 |
| 6 | DFDBA + 1.0 mg/ml rhPDGF | 29.9 ± 12.4 | 46.0 ± 23.0≠ | 26.0 ± 5.48 | 8.0 ± 13.04 |
| 7 | Sham Surgery, no graft | 27.4 ± 15.0 | 34.0 ± 27.0 | 48.0 ± 35.64 | 10.0 ± 22.4 |

*Groups 2 and 3 significantly greater ($p < 0.05$) than Groups 4 and 7.
**Group 1 significantly greater ($p < 0.05$) than Group 4.
†Group 2 significantly greater ($p < 0.05$) than Group 5.
‡Groups 2 and 3 significantly greater than Groups 1, 4 and 7.
≠Group 6 significantly greater than Group 4.

The mean percent periodontal regeneration (CNAA) in the surgery without grafts and surgery plus β-TCP alone groups were 27% and 37%, respectively. In contrast, β-TCP groups containing rhPDGF-BB exhibited significantly greater periodontal regeneration ($p<0.05$) than surgery without grafts or DFDBA alone (59% and 46% respectively for the 0.3 and 1.0 mg/ml concentrations versus 27% for surgery alone and 13% for DFDBA alone). Finally, the β-TCP group containing 0.3 mg/ml rhPDGF-BB demonstrated significantly greater periodontal regeneration ($p<0.05$) than the same concentration of rhPDGF-BB combined with allograft (59% versus 21%).

Bone fill was significantly greater ($p<0.05$) in the β-TCP+ 0.3 mg/ml rhPDGF-BB (84.0%) and the β-TCP+1.0 mg/ml rhPDGF-BB (74.2%) groups than in the β-TCP alone (28.0%), surgery alone (34%) or DFDBA alone (6%) treatment groups. There was also significantly greater bone fill ($p<0.05$) for the β-TCP+0.3 mg/ml rhPDGF-BB group compared to the DFDBA+0.3 mg/ml rhPDGF-BB group (84% and 20% respectively).

The group of analyses examining the 8-week data from the DFDBA groups and the surgery alone group (Groups 4, 5, 6, and 7) demonstrated no statistically significant differences between the DFDBA groups and surgery alone for periodontal regeneration (CNAA). There was a trend toward greater regeneration for those sites treated with the 1.0 mg/ml rhPDGF-BB enhanced DFDBA versus DFDBA alone. There was significantly greater bone fill ($p<0.05$) for sites treated with DFDBA+1.0 mg/ml rhPDGF-BB than DFDBA alone (46 and 6% respectively). There was a trend toward greater bone fill for sites treated with DFDBA containing 0.3 mg/ml rhPDGF-BB compared to DFDBA alone or surgery alone. However, sites treated with DFDBA alone demonstrated less bone fill into the defect than surgery alone (6 and 34%, respectively), with most of the defect being devoid of any fill or fill consisting of gingival (soft) connective tissue.

At four months following treatment, there remained significant differences in periodontal regeneration. β-TCP alone, as a result of extensive ankylosis, resulted in 36% regeneration, while the sites treated with β-TCP containing rhPDGF-BB had a mean regeneration of 58% and 49% in the 0.3 and 1.0 mg/ml rhPDGF-BB concentrations. Substantial bone fill was present in all three treatment groups. β-TCP alone resulted in 70% bone fill, β-TCP plus 0.3 mg/ml rhPDGF yielded 100% fill while the 1.0 mg/ml rhPDGF group had 75% fill.

D. Histologic Evaluation

Histologic evaluation was performed for all biopsies except one, in which evaluation was not possible due to difficulties encountered during processing.

Representative photomicrographs are shown in FIGS. 1A-G and 2A-C. FIG. 1A shows results from a site treated with surgery alone (no grafts). This specimen demonstrates limited periodontal regeneration (new bone (NB), new cementum (NC), and periodontal ligament (PDL)) as evidenced in the area of the notches and extending only a short distance coronally. The area of the furcation is occupied primarily by dense soft connective tissue (CT) with minimal new bone (NB) formation.

For sites treated with β-TCP alone (FIG. 1B) there is periodontal regeneration, similar to that observed for the surgery alone specimen, that extends from the base of the notches for a short distance coronally. As was seen in the surgery alone specimens, there was very little new bone formation with the greatest area of the furcation being occupied by soft connective tissue.

In contrast, FIG. 1C illustrates results obtained for sites treated with β-TCP+0.3 mg/ml rhPDGF-BB. Significant periodontal regeneration is shown with new bone, new cementum, and periodontal ligament extending along the entire surface of the furcation. Additionally, the area of the furcation is filled with new bone that extends the entire height of the furcation to the fornix.

Representative results for sites treated with β-TCP+1.0 mg/ml rhPDGF-BB are shown in FIG. 1D. While there is significant periodontal regeneration in the furcation, it does not extend along the entire surface of the furcation. There is new bone formation present along with soft connective tissue that is observed at the coronal portion of the defect along with a small space which is void of any tissue (VO) at the fornix of the furcation.

Figure 2:
FIGS. 2A-2C are photomicrographs showing the effect on bone formation 16 weeks following treatment.
Figure 2:
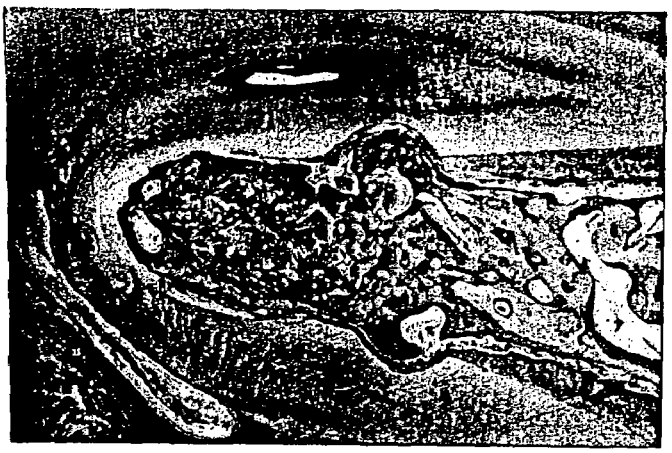
Figure 2:
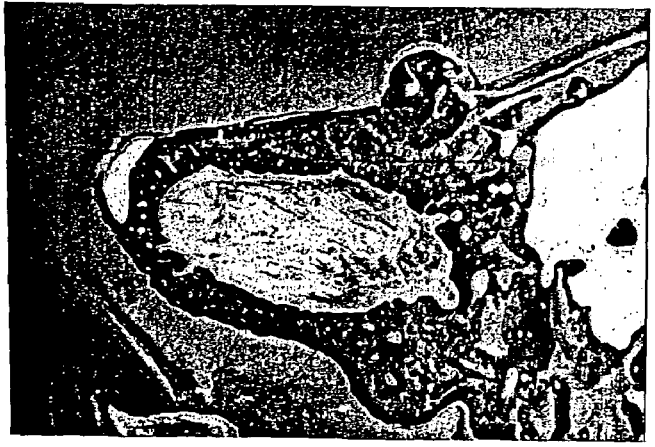

FIGS. 2A, 2B, and 2C illustrate results obtained for the allograft treatment groups. Representative results for the DFDBA alone group (FIG. 2A) shows very poor periodontal regeneration that is limited to the area of the notches extending only slightly in a coronal direction. New bone formation is limited and consists of small amounts of bone formation along the surface of residual DFDBA graft material (dark red staining along lighter pink islands). Additionally, the new bone is surrounded by extensive soft connective tissue that extends coronally to fill a significant area within the furcation. Finally, a large void space extends from the coronal extent of the soft connective tissue to the fornix of the furcation.

Histologic results for the DFDBA+0.3 and 1.0 mg/ml rhPDGF-BB are shown in FIGS. 2B and 2C, respectively. Both groups demonstrate greater periodontal regeneration compared to DFDBA alone with a complete new attachment apparatus (new bone, new cementum, and periodontal ligament) extending from the base of the notches in the roots for a short distance coronally (arrows). They also had greater bone fill within the area of the furcation, although there was significant fill of the furcation with soft connective tissue.

CONCLUSIONS

Based on the results of the study, treatment of a periodontal defect using rhPDGF-BB at either 0.3 mg/mL or 1.0 mg/mL in combination with a suitable carrier material (e.g., β-TCP) results in greater periodontal regeneration than the current products or procedures, such as grafts with β-TCP or bone allograft alone, or periodontal surgery without grafts.

Treatment with the 0.3 mg/mL and 1.0 mg/mL concentration of rhPDGF resulted in periodontal regeneration. The 0.3 mg/ml concentration of rhPDGF demonstrated greater periodontal regeneration and percent bone fill as compared to the 1.0 mg/ml concentration of rhPDGF when mixed with β-TCP.

β-TCP was more effective than allograft when mixed with rhPDGF-BB at any concentration. The new bone matured (remodeled) normally over time (0, 8, and 16 weeks) in all groups. There was no increase in ankylosis or root resorption in the rhPDGF groups. In fact, sites receiving rhPDGF-BB tended to have less ankylosis than control sites. This finding may result from the fact that rhPDGF-BB is mitogenic and chemotactic for periodontal ligament cells.

Materials and Methods

Materials Utilized: Test and Control Articles

The β-TCP utilized had a particle-size (0.25 mm-1.0 mm) that was optimized for periodontal use. Based on studies using a canine model, administered β-TCP is ~80% resorbed within three months and is replaced by autologous bone during the healing process.

The DFDBA was supplied by Musculoskeletal Transplant Foundation (MTF). The material was dog allograft, made by from the bones of a dog that was killed following completion of another study that tested a surgical procedure that was deemed to have no effect on skeletal tissues.

Recombinant hPDGF-BB was supplied by BioMimetic Pharmaceuticals and was manufactured by Chiron, Inc, the only supplier of FDA-approved rhPDGF-BB for human use. This rhPDGF-BB was approved by the FDA as a wound healing product under the trade name of Regranex®.

One ml syringes containing 0.5 ml of sterile rhPDGF-BB at two separate concentrations prepared in conformance with FDA standards for human materials and according to current applicable Good Manufacturing Processes (cGMP). Concentrations tested included 0.3 mg/ml and 1.0 mg/ml.

β-TCP was provided in vials containing 0.5 cc of sterile particles.

DFDBA was provided in 2.0 ml syringes containing 1.0 cc of sterile, demineralized freeze-dried dog bone allograft.

Material Preparation

At the time of the surgical procedure, the final implanted grafts were prepared by mixing the rhPDGF-BB solution with the matrix materials. Briefly, an amount of TCP or allograft sufficient to completely fill the osseous defect was placed into a sterile dish. The rhPDGF-BB solution sufficient to completely saturate the matrix was then added, the materials were mixed and allowed to sit on the surgical tray for about 10 minutes at room temperature prior to being placed in the osseous defect.

A 10 minute incubation time with the β-TCP material is sufficient to obtain maximum adsorption of the growth factor (see Appendix A). This is also an appropriate amount of time for surgeons in a clinical setting to have prior to placement of the product into the periodontal defect. Similarly, in a commercial market, the rhPDGF-BB and the matrix material can be supplied in separate containers in a kit and that the materials can be mixed directly before placement. This kit concept would greatly simplify product shelf life/stability considerations.

Example III

Use of PDGF for the Treatment of Periodontal Bone Defects in Humans

Recombinant human PDGF-BB (rhPDGF-BB) was tested for its effect on the regeneration of periodontal bone in human subjects. Two test groups were administered rhPDGF-BB at either 0.3 mg/mL (Group I) or 1.0 mg/mL (Group II). rhPDGF-BB was prepared in sodium acetate buffer and administered in a vehicle of beta-tricalcium phosphate (β-TCP). The control group, Group III, was administered β-TCP in sodium acetate buffer only.

The objective of clinical study was to evaluate the safety and effectiveness of graft material comprising β-TCP and rhPDGF-BB at either 0.3 mg/mL or 1.0 mg/mL in the management of one (1) to three (3) wall intra-osseous periodontal defects and to assess its regenerative capability in bone and soft tissue.

Study Design and Duration of Treatment

The study was a double-blind, controlled, prospective, randomized, parallel designed, multi-center clinical trial in subjects who required surgical intervention to treat a bone defect adjacent to the natural dentition. The subjects were randomized in equal proportions to result in three (3) treatment groups of approximately 60 subjects each (180 total). The duration of the study was six (6) months following implantation of the study device. The study enrolled 180 subjects.

Diagnosis and Main Entry Criteria

Male and female subjects, 25-75 years of age, with advanced periodontal disease in at least one site requiring surgical treatment to correct a bone defect were admitted to the study. Other inclusion criteria included: 1) a probing pocket depth measuring 7 mm or greater at the baseline visit; 2) after surgical debridement, 4 mm or greater vertical bone defect (BD) with at least 1 bony wall; 3) sufficient keratinized tissue to allow complete tissue coverage of the defect; and, 4) radiographic base of defect at least 3 mm coronal to the apex of the tooth. Subjects who smoked up to 1 pack a day and who had teeth with Class I & II furcation involvement were specifically allowed.

Dose and Mode of Administration

All treatment kits contained 0.25 g of β-TCP (an active control) and either 0.5 mL sodium acetate buffer solution alone (Group III), 0.3 mg/mL rhPDGF-BB (Group I), or 1.0 mg/mL rhPDGF-BB (Group II).

Following thorough debridement and root planing, the test solution was mixed with β-TCP in a sterile container, such that the β-TCP was fully saturated. Root surfaces were conditioned using either tetracycline, EDTA, or citric acid. The hydrated graft was then packed into the osseous defect and the tissue flaps were secured with interdental sutures to achieve complete coverage of the surgical site.

Effectiveness Measurement

The primary effectiveness measurement included the change in clinical attachment level (CAL) between baseline and six months post-surgery (Group I vs. Group III). The secondary effectiveness measurements consisted of the following outcomes: 1) linear bone growth (LBG) and % bone fill (% BF) from baseline to six months post-surgery based on the radiographic assessments (Group I and Group II vs. Group III); 2) change in CAL between baseline and six months post-surgery (Group II vs. Group III); 3) probing pocket depth reduction (PDR) between baseline and six months post-surgery (Group I and Group II vs. Group III); 4) gingival recession (GR) between baseline and six months post-surgery (Group I and Group II vs. Group III); 5) wound healing (WH) of the surgical site during the first three weeks post-surgery (Group I and Group II vs. Group III); 6) area under the curve for the change in CAL between baseline and three (3) and six (6) months (Group I and Group II vs. Group III); 7) the 95% lower confidence bound (LCB) for % BF at six (6) months post-surgery (Groups I, II, and III vs. demineralized freeze-dried bone allograft (DFDBA) as published in the literature; Parashis et al., J. Periodontol. 69:751-758, 1998); 8) the 95% LCB for linear bone growth at six (6) months post-surgery (Groups I, II, and III vs. demineralized freeze-dried bone allograft (DFDBA) as published in the literature; Persson et al., J. Clin. Periodontol. 27:104-108, 2000); 9) the 95% LCB for the change in CAL between baseline and six (6) months (Groups I, II, and II vs. EMDOGAIN®-PMA P930021, 1996); and 10) the 95% LCB for the change in CAL between baseline and six (6) months (Groups I, II and III vs. PEPGEN P-15™-PMA P990033, 1999).

Statistical Methods

Safety and effectiveness data were examined and summarized by descriptive statistics. Categorical measurements were displayed as counts and percents, and continuous variables were displayed as means, medians, standard deviations and ranges. Statistical comparisons between the test product treatment groups (Groups I and II) and the control (Group III) were made using Chi-Square and Fisher's Exact tests for categorical variables and t-tests or Analysis of Variance Methods (ANOVA) for continuous variables. Comparisons between treatment groups for ordinal variables were made using Cochran-Mantel-Haenszel methods. A p≦0.05 (one sided) was considered to be statistically significant for CAL, LBG and % BF.

Safety data were assessed by the frequency and severity of adverse events as evaluated clinically and radiographically. There were no significant differences between the three treatment groups at baseline. There were also no statistically significant differences observed in the incidence of adverse events (AEs; all causes) among the three treatment groups. The safety analysis did not identify any increased risk to the subject due to implantation of the graft material.

Summary of Effectiveness Results

The results from the statistical analyses revealed both clinically and statistically significant benefits for the two treatment groups (Groups I and II), compared to the active control of β-TCP alone (Group III) and historical controls including DFDBA, EMDOGAIN®, and PEPGENP-15™.

At three months post-surgery, a statistically significant CAL gain from baseline was observed in favor of Group I versus Group III (p=0.041), indicating that there are significant early benefits of PDGF on the gain in CAL. At six months post-surgery, this trend continued to favor Group I over Group III, although this difference was not statistically significant (p=0.200). The area under the curve analysis (AUC) which represents the cumulative effect (i.e. speed) for CAL gain between baseline and six months approached statistical significance favoring Group I in comparison to Group III (p=0.054). Further, the 95% lower confidence bound (LCB) analyses for all treatment groups substantiated the effectiveness of Groups I and II compared to the CAL gains observed at six (6) months for EMDOGAIN® and PEPGEN P-15™.

In addition to the observed clinical benefits of CAL, radiographic analyses including Linear Bone Growth (LBG) and Percent Bone Fill (% BF), revealed statistically significant improvement in bone gain for Groups I and II vs. Group III. % BF was defined as the percent of the original osseous defect filled with new bone as measured radiographically. LBG showed significant improvement in Group I (2.5 mm) when compared to Group III (0.9 mm, p<0.001). LBG was also significant for Group II (1.5 mm) when compared to Group III (p=0.021).

Percent Bone Fill (% BF) was significantly increased at six months post-surgical in Group 1 (56%) and Group II (34%) when compared to Group III (18%), for a p<0.001 and p=0.019, respectively. The 95% lower bound of the confidence interval at six months post-surgery, for both linear bone growth and % bone fill, substantiated the effectiveness of Groups I and II compared to the published radiographic results for DFDBA, the most widely used material for periodontal grafting procedures.

At three months, there was significantly less Gingival Recession (GR) (p=0.041) for Group I compared to Group III consistent with the beneficial effect observed with CAL. No statistically significant differences were observed in PDR and GR at six months. Descriptive analysis of the number of sites exhibiting complete wound healing (WH) at three weeks revealed improvements in Group I (72%) vs. Group II (60%) and Group III (55%), indicating a trend toward improved healing.

To assess the cumulative beneficial effect for clinical and radiographic outcomes, a composite effectiveness analysis was performed to determine the percent of patients with a successful outcome as defined by CAL>2.7 mm and LBG>1.1 mm at six (6) months. The CAL and LBG benchmarks of success were established by the mean levels achieved for these parameters by the implanted grafts, as identified in the "Effectiveness Measures" section above. The results showed that 61.7% of Group I patients and 37.9% of Group II patients met or exceeded the composite benchmark for success compared to 30.4% of Group III patients, resulting in a statistically significant benefit of Group I vs. Group III (p<0.001). % BF revealed similar benefits for Group I (70.0%) vs. Group III (44.6%) for p-value of 0.003.

In summary, Group I achieved statistically beneficial results for CAL and GR at three (3) months as well as LBG and % BF at six (6) months, compared to the β-TCP alone active control group (Group III). The clinical significance of these results is further confirmed by comparison to historical controls. It is concluded that PDGF-containing graft material was shown to achieve clinical and radiographic effectiveness by six months for the treatment of periodontal osseous defects.

TABLE 5

Summary of PDGF Graft Effectiveness

| ENDPOINT | | GROUP I | GROUP II | GROUP III |
|---|---|---|---|---|
| CAL Gain (mm): 3 months | | 3.8 | 3.4 | 3.3 |
| | | (p = 0.04) | (p = 0.40) | |
| CAL: AUC Analysis (mm × wk) | | 67.5 | 61.8 | 60.1 |
| | | (p = 0.05) | (p = 0.35) | |
| CAL (mm): 95% LCB 6 months (vs 2.7 mm for EMDOGAIN & 1.1 mm for PEPGEN) | | 3.3 | 3.2 | 3.1 |
| GR (mm): 3 months | | 0.5 | 0.7 | 0.9 |
| | | (p = 0.04) | (p = 0.46) | |
| LBG (mm): 6 months | | 2.5 | 1.5 | 0.9 |
| | | (p < 0.001) | (p = 0.02) | |
| % BF: 6 months | | 56.0 | 33.9 | 17.9 |
| | | (p < 0.001) | (p = 0.02) | |
| Composite Analysis (% Success) | CAL-LBG | 61.7% | 37.9% | 30.4% |
| | | (p < 0.001) | (p = 0.20) | |
| | CAL-% BF | 70.0% | 55.2% | 44.6% |
| | | (p = 0.003) | (p = 0.13) | |

Graft material (i.e., β-TCP) containing PDGF at 0.3 mg/mL and at 1.0 mg/mL was shown to be safe and effective in the restoration of alveolar bone and clinical attachment around teeth with moderate to advanced periodontitis in a large, randomized clinical trial involving 180 subjects studied for up to 6 months. These conclusions are based upon validated radiographic and clinical measurements as summarized below.

Consistent with the biocompatibility data of the PDGF-containing graft material, discussed above, and the historical safe use of each individual component (i.e., β-TCP alone or PDGF alone), the study revealed no evidence of either local or systemic adverse effects. There were no adverse outcomes attributable to the graft material, which was found to be safe.

CONCLUSION

Implantation of β-TCP containing PDGF at either 0.3 mg/mL or 1.0 mg/mL was found to be an effective treatment for the restoration of soft tissue attachment level and bone as shown by significantly improved CAL at 3 months compared to the active control. Our findings are also consistent with the AUC analysis that showed an improvement in CAL gain between baseline and six months. Implantation of β-TCP containing PDGF at either 0.3 mg/mL or 1.0 mg/mL was also found to be an effective treatment based on significantly improved LBG and % BF compared to the active control. Significantly improved clinical outcomes as shown by the composite analysis of both soft and hard tissue measurements compared to the β-TCP alone active control also demonstrate the effectiveness of the treatment protocol described above. Finally, the results of administering β-TCP containing PDGF at either 0.3 mg/mL or 1.0 mg/mL were found to exceed established benchmarks of effectiveness both clinically and radiographically.

The results of this trial together with extensive and confirmatory data from in vitro, animal and human studies demonstrate that PDGF-containing graft material stimulates soft and hard tissue regeneration in periodontal defects, although the effects were more significant when PDGF in the range of 0.1 to 1.0 mg/mL (e.g., 0.1 mg/mL, 0.3 mg/mL, or 1.0 mg/mL) was administered in the graft material. Moreover, PDGF administered in the graft material in the amount of 0.3 mg/mL effectively regenerated soft tissue and bone.

Other embodiments are within the following claims.

What is claimed is:

1. An implant material consisting of a porous calcium phosphate having incorporated therein a liquid consisting of platelet derived growth factor (PDGF) at a concentration in a range of about 0.1 mg/mL to about 1.0 mg/mL in a buffer, wherein the calcium phosphate has interconnected pores, a porosity greater than 40%, and consists of particles in a range of about 100 microns to about 5000 microns in size.

2. The implant material of claim 1 wherein the PDGF is recombinant PDGF.

3. The implant material of claim 1 wherein the PDGF is recombinant PDGF-BB.

4. The implant material of claim 1 wherein the liquid consists of PDGF at a concentration of about 0.3 mg/mL in a buffer.

5. The implant material of claim 1 wherein the liquid consists of PDGF at a concentration in a range of about 0.25 mg/mL to about 0.5 mg/mL in a buffer.

6. The implant material of claim 1 wherein the calcium phosphate is tricalcium phosphate.

7. The implant material of claim 1 wherein the calcium phosphate consists of particles in a range of about 100 microns to about 3000 microns in size.

8. The implant material of claim 1 wherein the calcium phosphate consists of particles in a range of about 250 microns to about 1000 microns in size.

9. The implant material of claim 1 wherein the implant material is resorbable such that at least 80% of the calcium phosphate is resorbed within one year of being implanted.

10. The implant material of claim 1 wherein the incorporated liquid is adsorbed or absorbed to the calcium phosphate.

11. An implant material consisting of a calcium phosphate having incorporated therein a liquid consisting of platelet derived growth factor (PDGF) at a concentration in a range of about 0.1 mg/mL to about 1.0 mg/mL in a buffer, wherein the implant material is a composition having a porosity that facilitates cell migration into the composition and the calcium phosphate has interconnected pores and consists of particles in a range of about 100 microns to about 5000 microns in size.

12. The implant material of claim 11 wherein said porosity is macroporosity.

13. The implant material of claim 11 wherein said porosity consists of porous calcium phosphate particles having a porosity greater than 40%.

14. The implant material of claim 11 wherein the PDGF is recombinant human (rh) PDGF-BB.

15. The implant material of claim 11 wherein the calcium phosphate is tricalcium phosphate.

16. The implant material of claim 11 wherein the calcium phosphate consists of particles in a range of about 100 microns to about 3000 microns in size.

17. The implant material of claim 11 wherein the calcium phosphate consists of particles in a range of about 250 microns to about 2000 microns in size.

18. The implant material of claim 11 wherein the calcium phosphate consists of particles in a range of about 250 microns to about 1000 microns in size.

19. The implant material of claim 11 wherein the liquid consists of PDGF at a concentration of about 0.3 mg/mL in a buffer.

20. The implant material of claim 11 wherein the liquid consists of PDGF at a concentration in a range of about 0.25 mg/mL to about 0.5 mg/mL in a buffer.

21. The implant material of claim 11 wherein the liquid consists of PDGF at a concentration in a range of about 0.2 mg/mL to about 0.75 mg/mL in a buffer.

22. The implant material of claim 11 wherein the implant material is resorbable such that at least 80% of the calcium phosphate is resorbed within one year of being implanted.

23. An implant material consisting of collagen and a porous calcium phosphate having incorporated therein a liquid consisting of platelet derived growth factor (PDGF) at a concentration in a range of about 0.1 mg/mL to about 1.0 mg/mL in a buffer, wherein the calcium phosphate has interconnected pores, a porosity greater than 40%, and consists of particles in a range of about 100 microns to about 5000 microns in size.

24. The implant material of claim 23 wherein the PDGF is recombinant human (rh) PDGF-BB and the calcium phosphate is tricalcium phosphate.

25. The implant material of claim 23 wherein the calcium phosphate consists of particles in a range of about 100 microns to about 3000 microns in size.

26. The implant material of claim 23 wherein the calcium phosphate consists of particles in a range of about 250 microns to about 1000 microns in size.

27. The implant material of claim 23 wherein the liquid consists of PDGF at a concentration of about 0.3 mg/mL in a buffer.

28. The implant material of claim 23 wherein the implant material is resorbable such that at least 80% of the calcium phosphate is resorbed within one year of being implanted.

29. An implant material consisting of collagen and a calcium phosphate having incorporated therein a liquid consisting of platelet derived growth factor (PDGF) at a concentration in a range of about 0.1 mg/mL to about 1.0 mg/mL in a buffer, wherein the implant material is a composition having a porosity that facilitates cell migration into the composition and the calcium phosphate has interconnected pores and consists of particles in a range of about 100 microns to about 5000 microns in size.

30. The implant material of claim 29 wherein said porosity is macroporosity.

31. The implant material of claim 29 wherein said porosity consists of porous calcium phosphate particles having a porosity greater than 40%.

32. The implant material of claim 29 wherein the PDGF is recombinant human (rh) PDGF-BB and the calcium phosphate is tricalcium phosphate.

33. The implant material of claim 29 wherein the calcium phosphate consists of particles in a range of about 100 microns to about 3000 microns in size.

34. The implant material of claim 29 wherein the calcium phosphate consists of particles in a range of about 250 microns to about 1000 microns in size.

35. The implant material of claim 29 wherein the liquid consists of PDGF at a concentration of about 0.3 mg/mL in a buffer.

36. An implant material consisting of a calcium phosphate having incorporated therein a liquid consisting of platelet derived growth factor (PDGF) at a concentration in a range of about 0.1 mg/mL to about 1.0 mg/mL in a buffer, wherein the calcium phosphate has interconnected pores and consists of particles in a range of about 100 microns to about 5000 microns in size, and wherein the calcium phosphate is capable of absorbing an amount of the liquid consisting of PDGF that is equal to at least about 25% of the calcium phosphate's own weight.

37. The implant material of claim 36, wherein the calcium phosphate is capable of absorbing an amount of the liquid consisting of PDGF that is equal to at least about 50% of the calcium phosphate's own weight.

38. The implant material of claim 37, wherein the calcium phosphate is capable of absorbing an amount of the liquid consisting of PDGF that is equal to at least about 200% of the calcium phosphate's own weight.

39. The implant material of claim 38, wherein the calcium phosphate is capable of absorbing an amount of the liquid consisting of PDGF that is equal to at least about 300% of the calcium phosphate's own weight.

40. An implant material consisting of collagen and a calcium phosphate having incorporated therein a liquid consisting of platelet derived growth factor (PDGF) at a concentration in a range of about 0.1 mg/mL to about 1.0 mg/mL in a buffer, wherein the calcium phosphate has interconnected pores and consists of particles in a range of about 100 microns to about 5000 microns in size, and wherein the calcium phosphate and collagen are capable of absorbing an amount of the liquid consisting of PDGF that is equal to at least about 25% of the weight of the calcium phosphate and collagen.

41. The implant material of claim 40, wherein the calcium phosphate and collagen are capable of absorbing an amount of the liquid consisting of PDGF that is equal to at least about 50% of the weight of the calcium phosphate and collagen.

42. The implant material of claim 41, wherein the calcium phosphate and collagen are capable of absorbing an amount of the liquid consisting of PDGF that is equal to at least about 200% of the weight of the calcium phosphate and collagen.

43. The implant material of claim 42, wherein the calcium phosphate and collagen are capable of absorbing an amount of the liquid consisting of PDGF that is equal to at least about 300% of the weight of the calcium phosphate and collagen.

44. An implant material consisting of a calcium phosphate having incorporated therein a liquid consisting of platelet derived growth factor (PDGF) at a concentration of about 0.3 mg/mL in a buffer, wherein the calcium phosphate has interconnected pores and consists of particles in a range of about 100 microns to about 5000 microns in size, and wherein the calcium phosphate is capable of absorbing an amount of the liquid consisting of PDGF that is equal to at least about 25% of the calcium phosphate's own weight.

45. An implant material consisting of collagen and a calcium phosphate having incorporated therein a liquid consisting of platelet derived growth factor (PDGF) at a concentration of about 0.3 mg/mL in a buffer, wherein the calcium phosphate has interconnected pores and consists of particles in a range of about 100 microns to about 5000 microns in size, and wherein the calcium phosphate and collagen are capable of absorbing an amount of the liquid consisting of PDGF that is equal to at least about 25% of the weight of the calcium phosphate and collagen.

* * * * *